(12) United States Patent
Norton

(10) Patent No.: US 9,308,162 B2
(45) Date of Patent: Apr. 12, 2016

(54) BIOCOMPATIBLE OLIGOMER-POLYMER COMPOSITIONS

(75) Inventor: Richard L. Norton, Ft. Collins, CO (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 411 days.

(21) Appl. No.: 12/995,910

(22) PCT Filed: Jun. 3, 2009

(86) PCT No.: PCT/US2009/003363
§ 371 (c)(1),
(2), (4) Date: Mar. 3, 2011

(87) PCT Pub. No.: WO2009/148581
PCT Pub. Date: Dec. 10, 2009

(65) Prior Publication Data
US 2011/0245172 A1    Oct. 6, 2011

Related U.S. Application Data

(60) Provisional application No. 61/058,458, filed on Jun. 3, 2008.

(51) Int. Cl.
*A61K 9/00* (2006.01)
*A61K 47/08* (2006.01)
*A61K 47/34* (2006.01)
*C08L 67/04* (2006.01)

(52) U.S. Cl.
CPC ............... *A61K 9/0024* (2013.01); *A61K 47/08* (2013.01); *A61K 47/34* (2013.01); *C08L 67/04* (2013.01)

(58) Field of Classification Search
None
See application file for complete search history.

(56) References Cited

U.S. PATENT DOCUMENTS

| 2,371,281 | A | | 3/1945 | Claborn | |
|---|---|---|---|---|---|
| 6,126,919 | A | * | 10/2000 | Stefely et al. | 424/45 |
| 6,565,874 | B1 | * | 5/2003 | Dunn et al. | 424/426 |
| 6,815,469 | B1 | * | 11/2004 | Voelkel et al. | 523/105 |
| 7,033,608 | B1 | * | 4/2006 | Jevanthi et al. | 424/490 |
| 2004/0001889 | A1 | * | 1/2004 | Chen et al. | 424/468 |
| 2004/0024069 | A1 | * | 2/2004 | Chen et al. | 514/772.3 |
| 2007/0280992 | A1 | * | 12/2007 | Margaron | A61F 9/0008 424/426 |

FOREIGN PATENT DOCUMENTS

| DE | 1020324 | 12/1957 |
|---|---|---|
| EP | 1586309 | 10/2005 |
| WO | WO-2009148581 A1 | 12/2009 |

OTHER PUBLICATIONS

Ferguson et al., Solubility and Molecular Conformations of n-alkane Chains in Water, J. Phys. Chem. B 2009, 113, 6405-6414.*
Huang & Goh, Interpolymer Complexes through Hydrophobic Interactions: C60-End-Capped Poly(ethylene oxide)/Poly(methacrylic acid) Complexes, Macromolecules, 2000, 33, 8894-8897.*
von Burkersroda et al., Why degradable polymers undergo surface erosion or bulk erosion, Biomaterials 23 (2002) 4221-4231.*
"International Application Serial No. PCT/US2009/003363, Search Report mailed Oct. 21, 2009".
"International Application Serial No. PCT/US2009/003363, Written Opinion mailed Oct. 21, 2009".
Jeon, Nan Jung, et al., "Synthesis of alkyl (R)-lactates and alkyl (S,S)-O-lactyllactates by alcoholysis of rac-lactide using Novozym 435", Tetrahedron Letters, 47(37), (Sep. 11, 2006), 6517-6520.
Rehberg, C. E, et al., "Esters of Lactyllactic Acid", Journal of the American Chemical Society, 74(6), (Mar. 20, 1952), 1609-1609.
"European Application Serial No. 09758745.5, Response filed Jun. 30, 2014 to Office Action filed Feb. 14, 2014", 31 pgs.
"International Application Serial No. PCT/US2009/003363, International Preliminary Report on Patentability mailed Dec. 16, 2010", 7 pgs.
"European Application Serial No. 09758745.5, Examination Notification Art. 94(3) mailed Feb. 14, 2014", 3 pgs.

* cited by examiner

*Primary Examiner* — Karlheinz R Skowronek
*Assistant Examiner* — Joseph Fischer
(74) *Attorney, Agent, or Firm* — Schwegman Lundberg & Woessner, P.A.

(57) ABSTRACT

The present invention relates to biocompatible oligomer-polymer compositions for the in situ formation of implants, wherein the implants release a bioactive agent, a metabolite, or a prodrug thereof, at a controlled rate. The sustained release delivery system includes a flowable composition containing a bioactive agent, a metabolite, or a prodrug thereof, and an implant containing a bioactive agent, a metabolite, or a prodrug thereof. The flowable composition may be injected into tissue whereupon it coagulates to become the solid or gel, monolithic implant. The flowable composition includes a biodegradable, thermoplastic polymer, a biocompatible end-capped oligomeric liquid, and a bioactive agent, a metabolite, or a prodrug thereof.

16 Claims, No Drawings

BIOCOMPATIBLE OLIGOMER-POLYMER COMPOSITIONS

CROSS-REFERENCE TO RELATED APPLICATIONS

This application is a nationalization under 35 U.S.C. 371 of PCT/US2009/003363, filed Jun. 3, 2009 and published as WO 2009/148581 A1 on Dec. 10, 2009, which claims priority to U.S. Provisional Application Ser. No. 61/058,458, filed Jun. 3, 2008, which applications are incorporated herein by reference in its entirety.

FIELD OF THE INVENTION

The field of invention is biocompatible oligomer-polymer compositions for the in situ formation of implants, wherein the implants release a bioactive agent, a metabolite, or a prodrug thereof, at a controlled rate.

BACKGROUND OF THE INVENTION

Compositions adapted for use in controlled release delivery systems, such as biodegradable and bioerodible implants, are well known. Such controlled release systems are in general advantageous as they provide for the controlled and sustained release of medications, often directly at or near the desired site of action, over the period of days, weeks or even months.

Controlled release systems include polymer matrices that are known to be broken down in the body by various endogenous substances such as enzymes and water, such as polyesters including poly-lactide, poly-glycolide, polycaprolactone, and copolymers thereof, as well as capped versions using $C_1$ to $C_{10}$ mono-alkanols and chain-extended versions using $C_2$ to $C_{30}$ diols and polyols. Especially preferred are the "PLG copolymers" prepared from glycolide (1,4-dioxan-2,5-dione, glycolic acid cyclic dimer lactone) and lactide (3,6-dimethyl-1,4-dioxan-2,5-dione, lactic acid cyclic dimer lactone) as well as the capped and chain extended versions thereof. These copolymer materials are particularly favored for this application due to their facile breakdown in vivo by water or enzymes in the body to non-toxic materials, and their favorable properties in temporally controlling the release of biologically active agents ("bioactive agents") that may be contained within a mass of the polymer.

These controlled release systems are typically prepared with a biocompatible polar aprotic organic liquid, injected into the body of a patient, and the biocompatible polar aprotic organic liquid dissipates to produce a solid or gel biodegradable implant. However, some biocompatible polar aprotic organic liquids may have unfavorable toxicological properties and/or cause irritation to the patient.

There is a continuing need to develop liquids, which have favorable toxicological properties and do not cause irritation to the patient, for the in situ formation of implants.

SUMMARY OF THE INVENTION

The present invention provides biocompatible oligomer-polymer compositions for the in situ formation of implants, wherein the implants release a bioactive agent, a metabolite, or a prodrug thereof, at a controlled rate. These compositions include biocompatible end-capped oligomeric liquids that are useful for forming implants in situ because they have very good biocompatibility and low toxicity. These biocompatible end-capped oligomeric liquids are effective for dissolving a specific polymer, have some degree of water solubility, and can be custom tailored to dissolve a particular active pharmaceutical ingredient. By being end-capped oligomers of, for example, lactide, glycolide, lactic acid, and/or glycolic acid, these biocompatible oligomeric liquids are readily degraded by the body through hydrolysis to yield compounds with known and acceptable toxicological characteristics.

The biocompatible end-capped oligomeric liquids prepared herein may be used to prepare two syringe ATRIGEL® formulations and are especially advantageous in preparing single syringe ATRIGEL® formulations because they are not reactive with the polymer and/or the drug and will inhibit water from entering the ATRIGEL® formulation. The biocompatible end-capped oligomeric liquids have similar chemical structures as the implant polymer and will react with any water that may be present in the formulation and thereby increase the storage life of the ATRIGEL® product. Further, unlike the biocompatible end-capped oligomeric liquids disclosed by Voelkel et al. in U.S. Pat. No. 6,815,469, which possess free carboxyl and free hydroxyl groups that may react with the implant polymer, the biocompatible end-capped oligomeric liquids described herein are more hydrophobic and offer better solubility and stability for the implant polymer.

In one embodiment, a flowable composition is provided including: (a) a biodegradable thermoplastic polymer that is at least substantially insoluble in body fluid; (b) a biocompatible end-capped oligomeric liquid; and (c) a bioactive agent, a metabolite, or a prodrug thereof. The biocompatible end-capped oligomeric liquid is of the formula I, II, III, IV, or V:

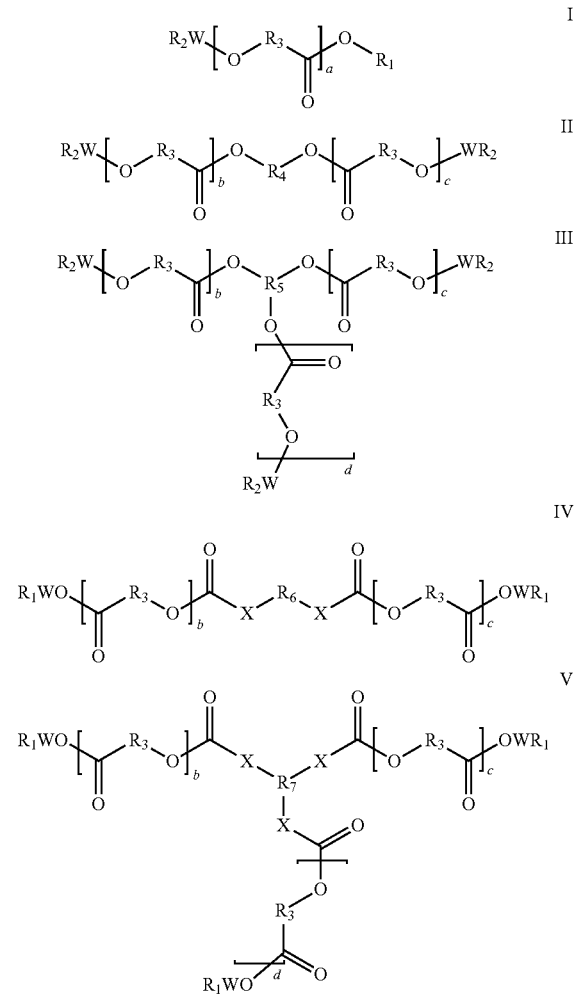

wherein:
each $R_1$ is independently hydrogen, $(C_1-C_{12})$alkyl, or $(C_1-C_{12})$alkylenecarboxylic$(C_1-C_{12})$alkylester;
each $R_2$ is independently hydrogen, $(C_1-C_{12})$alkyl, carbonyl$(C_1-C_{12})$alkyl, carboxylic$(C_1-C_{12})$alkylester, or carboxylic$(C_1-C_{12})$alkylester, wherein $R_2$ in not hydrogen in Formula I if W is absent, and further wherein at least one $R_2$ is not hydrogen in Formulas II and III if W is absent;
each $R_3$ is independently $(C_1-C_{12})$alkylene;
$R_4$ is $(C_1-C_2)$alkylene, carbonyl$(C_1-C_{12})$alkylcarbonyl, or $(C_3-C_{12})$cycloalkadiyl;
$R_5$ is $(C_1-C_{12})$alkatriyl or $(C_3-C_{12})$cycloalkatriyl;
$R_6$ is $(C_1-C_{12})$alkylene, $(C_1-C_{12})$alkyne, $(C_3-C_{12})$cycloalkadiyl, $(C_1-C_{12})$alkatriyl, or $(C_3-C_{12})$cycloalkatriyl;
$R_7$ is $(C_1-C_{12})$alkylene or $(C_1-C_{12})$alkatriyl,
X is absent or oxygen;
W is absent, carbonyl, carbonyloxy, or oxycarbonyl; and
any alkyl or alkylene of $R_1$, $R_2$, $R_3$, $R_4$, $R_5$, $R_6$ and $R_7$ can optionally be substituted on carbon with one or more oxo, hydroxy, halogen, nitro, cyano, $(C_1-C_{12})$alkyl, $(C_1-C_6)$alkoxy, trifluoromethyl, and optionally interrupted on carbon with one or more oxy, imino, or thio, and is optionally partially unsaturated; and
each a, b, c, and d is independently 0, 1, 2, 3, 4, or 5.

The biocompatible end-capped oligomeric liquid is a liquid at ambient temperature. Accordingly, any particular species set out by the foregoing formulas that is not a liquid at or near ambient temperature is excluded. It is believed that all species set out by the foregoing formulas are liquids at ambient temperature or near ambient temperature.

In one embodiment, each $R_1$ is independently hydrogen, —$(CH_2)_mCH_3$, —$CH_2CH_2(OCH_2CH_2)_mO(CH_2)_nCH_3$, —$CH_2CH_2(OCH_2CH_2)_mOCOCH_3$, —$CH_2COOY$, —$CH(CH_3)COOY$, —$CH_2CH_2COOY$, —$CH_2CH_2CH_2COOY$, —$CH_2CH_2CH_2CH_2COOY$, —$CH_2CH_2CH_2CH_2CH_2COOY$, —$CH_2CH(CH_3)Y$, or -(cyclo$C_6H_{11}$), wherein each m and n is independently 0, 1, 2, 3, 4, 5, 6, or 7;
each $R_2$ is independently hydrogen, —$CH_3$, —$CH_2CH_3$, —$(CH_2)_oCH_3$, —$CH_2CH_2(OCH_2CH_2)_oOCH_3$, —$CH_2CH_2(OCH_2CH_2)_oOCH_2CH_3$, —$CH_2CH_2(OCH_2CH_2)_oOCOCH_3$, —$COCH_3$, —$CO(CH_2)_oCH_3$, —$COO(CH_2)_oCH_3$, or —$CO(OCH_2CH_2)_oCH_3$, wherein o is 0, 1, 2, 3, 4, 5, 6, or 7, wherein $R_2$ in not hydrogen in Formula I if W is absent, and further wherein at least one $R_2$ is not hydrogen in Formulas II and III if W is absent;
each $R_3$ is independently —$(CH_2)_p$—, —$CH(CH_3)$—, —$(CH_2CH_2O)_pCH_2$—, —$(CH(CH_3)CH_2)$—, or —$(CH(CH_2CH_3)CH_2)$—, wherein p is 0, 1, 2, 3, 4, 5, 6, or 7,
$R_4$ is —$(CH_2)_q$—, —$CO(CH_2)_qCO$—, —$(CH_2CH_2O)_qCH_2CH_2$—, —$CH_2CH_2CH_2CH_2CH_2CH_2$—, —$(CH_2)_qCH(CH_3)$—, —$((CH_2)_qO)_q$—, —$CH_2CH(Y)CH_2$—, cyclohexane-1,2-diyl, cyclohexane-1,3-diyl or cyclohexane-1,4-diyl, wherein q is 1, 2, 3, 4, 5, 6, or 7;
$R_5$ is (—$CH_2)_2CH$—, (—$CH_2)_3CCH_3$, (—$CH_2)_3CCH_2CH_3$, or 1,2,6-hexanetriyl;
$R_6$ is —CH=CH—, —$(CH_2)_r$—, —$O(CH_2CH_2O)_r$— wherein r is 1, 2, 3, 4, 5, 6, or 7;
$R_7$ is (—$CH_2)_2CH$—, (—$CH_2)_2COH$—, (—$CH_2)(—CHOH)CH$—, (—$CH_2)(—CO)CH$—, or (—$CH_2)(—CH$=$)C$—;
X is absent or oxygen;
W is absent, —CO—, —COO—, or —OCO—; and
Y is —$CH_3$, —$C_2H_5$, —$C_3H_7$, or —$C_4H_9$.

In one embodiment, each $R_1$ is independently hydrogen, —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$CH_2CH_2(OCH_2CH_2)_2OCH_3$, —$CH_2CH_2(OCH_2CH_2)_2OCH_2CH_3$, or —$CH_2CH_2(OCH_2CH_2)_2OCOCH_3$;
each $R_2$ is independently hydrogen, —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$CH_2CH_2(OCH_2CH_2)_2OCH_3$, —$CH_2CH_2(OCH_2CH_2)_2OCH_2CH_3$, or —$CH_2CH_2(OCH_2CH_2)_2OCOCH_3$, wherein $R_2$ in not hydrogen in Formula I if W is absent, and further wherein at least one $R_2$ is not hydrogen in Formulas II and III if W is absent;
each $R_3$ is independently —$CH_2$—, —$(CH_2)_2$—, —$(CH_2)_3$—, —$(CH_2)_4$—, —$(CH_2)_5$—, —$(CH_2)_6$—, —$(CH_2)_7$—, —$CH(CH_3)$—, —$(CH(CH_3)CH_2)$—, —$(CH(CH_2CH_3)CH_2)$—,
or
—$(CH_2CH_2OCH_2)$—;
$R_4$ is —$(CH_2)_3$—, —$(CH_2)_4$—, —$(CH_2)_5$—, —$(CH_2)_6$—, —$COCH_2CO$—, —$CO(CH_2)_2CO$—, —$CO(CH_2)_3CO$—, —$CO(CH_2)_4CO$—, —$CO(CH_2)_5CO$—, —$CO(CH_2)_6CO$—, —$CO(CH_2)_7CO$—, —$CO(CH_2)_8CO$—, —$(CH_2CH_2O)_2CH_2CH_2$—, —$(CH_2CH_2O)_3CH_2CH_2$—, —$(CH_2CH_2O)_4CH_2CH_2$—, —$(CH_2CH_2O)_5CH_2CH_2$—, —$(CH_2CH_2O)_6CH_2CH_2$—, or —$CH_2CH_2CH_2CH_2CH_2CH_2$—;
$R_5$ is (—$CH_2)_2CH$—;
$R_6$ is —CH=CH—, —$(CH_2)$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$O(CH_2CH_2O)$—, —$O(CH_2CH_2O)_2$—, —$O(CH_2CH_2O)_3$—, —$O(CH_2CH_2O)_4$—, —$O(CH_2CH_2O)_5$—, or —$O(CH_2CH_2O)_6$—;
$R_7$ is (—$CH_2)_2CH$—, (—$CH_2)_2COH$—, (—$CH_2)(—CHOH)CH$—, (—$CH_2)(—CO)CH$—, or (—$CH_2)(—CH$=$)C$—;
X is absent or oxygen;
W is absent, —CO—, —COO—, or —OCO—; and
each a, b, c, and d is independently 0, 1, 2, 3, or 4.

In one embodiment, the biocompatible end-capped oligomeric liquid is present in about 10 wt. % to about 90 wt. % of the composition, or preferably the biocompatible end-capped oligomeric liquid is present in about 30 wt. % to about 70 wt. % of the composition.

The biodegradable thermoplastic polymer may be a homopolymer, a copolymer or a terpolymer of repeating monomeric units linked by such groups as ester groups, anhydride groups, carbonate groups, amide groups, urethane groups, urea groups, ether groups, esteramide groups, acetal groups, ketal groups, orthocarbonate groups and any other organic functional group that can be hydrolyzed by enzymatic or hydrolytic reaction (i.e., is biodegradable by hydrolytic action). The preferred thermoplastic polymer, polyester, may be composed of units of one or more hydroxycarboxylic acid residues or diol and dicarboxylic acid residues, wherein the distribution of differing residues may be random, block, paired or sequential.

In one embodiment, the biodegradable thermoplastic polymer is a polyester of one or more $C_2$ to $C_{10}$ hydroxycarboxylic acids optionally chain extended such as for example with a $C_2$ to $C_{10}$ diol, a polyester of a combination of one or more $C_2$ to $C_{12}$ diols and one or more $C_3$ to $C_{12}$ dicarboxylic acids, a polyester of a combination of one or more $C_3$ to $C_{12}$ triols and one or more $C_3$ to $C_{12}$ dicarboxylic acids, or a combination thereof.

In one embodiment, the hydroxy carboxylic acid or acids are in the form of dimers.

In one embodiment, the polyester is a polylactide, a polyglycolide, a polycaprolactone, a copolymer thereof, a terpolymer thereof, or a combination thereof.

In one embodiment, the biodegradable thermoplastic polyester is a 50/50, 55/45, 65/35, 75/25, 85/15, 90/10, or 95/5 poly(DL-lactide-co-glycolide) having a carboxy terminal group, or is a 50/50, 55/45, 75/25, 85/15, 90/10, or 95/5 poly(DL-lactide-co-glycolide) without a carboxy terminal group (e.g., capped with a $C_1$ to $C_{10}$ mono-alcohol), and optionally the polyester without a terminal carboxyl group is extended with a $C_2$ to $C_{12}$ diol.

In one embodiment, the biodegradable thermoplastic polyester is present in about 10 wt. % to about 95 wt. %, or about 20 wt. % to about 70 wt. %, or preferably, from about 30 wt. % to about 60 wt. % of the composition, and optionally the biodegradable thermoplastic polyester has an average molecular weight of from about 10,000 to about 45,000 Daltons, preferably about 15,000 to about 40,000 Daltons.

In one embodiment, the biodegradable thermoplastic polymer is a non-hydrolyzed PLG low-burst copolymer polyester material having a weight average molecular weight of about 10 kilodaltons to about 50 kilodaltons, a polydispersity index of about 1.4 to about 2.0, and from which a copolymer fraction characterized by a weight average molecular weight of about 4 kDa to about 10 kDa and a polydispersity index of about 1.4 to about 2.5 has been removed, as is disclosed in U.S. Patent Application Ser. No. 60/901,435.

In one embodiment, the biodegradable thermoplastic polymer is a purified poly(DL-lactide-co-glycolide) (PLG) prepared by extracting poly(DL-lactide-co-glycolide), having an average molecular weight (Mw) of about 15 kDa to about 45 kDa, with carbon dioxide at a temperature above about 40° C. and a pressure above about 1,000 psi. This purified poly(DL-lactide-co-glycolide) has a narrower molecular weight distribution than the poly(DL-lactide-co-glycolide). This purified poly(DL-lactide-co-glycolide) includes less than about 5 wt. % of oligomers, having a molecular weight of up to about 5 kDa. The purified poly(DL-lactide-co-glycolide) also includes less than about 5 wt. % of monomers. The purified poly(DL-lactide-co-glycolide) includes less than about 5 wt. % of poly(DL-lactide-co-glycolide) having a molecular weight of at least about 55 kDa, as is disclosed in U.S. Patent Application Ser. No. 60/850,744.

In one embodiment, the biodegradable thermoplastic polymer is a purified PLGH of the PLGH(p) type that has been purified by solvent precipitation and includes the addition of about 5 wt % of a PLG oligomer, for example, of a polylactide or of 65/35 poly(lactide-glycolide) material having an average molecular weight of about 5-10 kDa and lacking free carboxylic acid groups, as is disclosed in copending U.S. Patent Application Ser. No. 61/058,477.

The bioactive agent may be any pharmaceutical small molecule or biological compound that causes a pharmacological, biological and/or physiological effect when administered to a mammal such as a human. The effect may be intrinsic in that it ameliorates, prevents, minimizes or otherwise treats an organic malcondition of the mammal, or the effect may be extrinsic in that it ameliorates, prevents, minimizes or otherwise treats a malcondition of the mammal caused by an exogenous agent.

In one embodiment, the bioactive agent, a metabolite, or a prodrug thereof, includes a hormone, an immunomodulator, an immunosuppressant, an antibiotic, a cytostatic, a diuretic, a gastrointestinal agent, a cardiovascular agent, a neuropharmaceutical, or a combination thereof.

In one embodiment, the bioactive agent, a metabolite, or a prodrug thereof, includes leuprolide, octreotide, brimonidine, latanoprost, latanoprost acid, travoprost, travoprost acid, brinzolamide, dorzolamide, betaxolol, terbinafine, risperidone, rapamycin, or a combination thereof.

In one embodiment, the bioactive agent, a metabolite, or a prodrug thereof, is present in about 0.5 wt. % to about 50 wt. % of the composition, or preferably the bioactive agent, a metabolite, or a prodrug thereof, is present in about 1 wt. % to about 30 wt. % of the composition.

In some embodiments, the flowable composition described herein is used in the manufacture of a medicament for treatment of a malcondition, disorder or disease of the mammal.

In one embodiment, a flowable composition is provided further including a biocompatible polar aprotic organic liquid wherein the biocompatible polar aprotic organic liquid includes an amide, an ester, a carbonate, a ketone, an ether, a sulfonyl, or any combination thereof, and wherein the biocompatible polar aprotic liquid has a solubility in aqueous medium or body fluid ranging from insoluble to completely soluble in all proportions.

In one embodiment, a flowable composition is provided further including a biocompatible polar aprotic organic liquid including N-methyl-2-pyrrolidone, 2-pyrrolidone, N,N-dimethylformamide, dimethyl sulfoxide, propylene carbonate, caprolactam, triacetin, or any combination thereof.

In one embodiment, a flowable composition is provided that is an injectable subcutaneous formulation, and optionally has a volume of about 0.20 mL to about 2.0 mL, or preferably has a volume of about 0.30 mL to about 1.0 mL.

In one embodiment, a flowable composition is provided that is formulated for administration about once per month, or preferably is formulated for administration about once per three months, or more preferably is formulated for administration about once per four months to about once per six months.

In one embodiment, a flowable composition is provided having the property of production of minimal tissue necrosis when injected subcutaneously.

In one embodiment, a flowable composition is provided having a substantially linear cumulative release profile after one day.

In one embodiment, a method for forming a flowable composition is provided for use as a controlled release implant, including the step of mixing, in any order: (a) a biodegradable thermoplastic polymer that is at least substantially insoluble in aqueous medium or body fluid; (b) a biocompatible end-capped oligomeric liquid; and (c) a bioactive agent, a metabolite, or a prodrug thereof, wherein the mixing is performed for a sufficient period of time effective to form the flowable composition for use as a controlled release implant.

In one embodiment, a biodegradable implant is formed in situ, in a patient, by the steps including: (a) injecting the flowable composition into the body of the patient; and (b) allowing the biocompatible end-capped oligomeric liquid to dissipate to produce a solid or gel biodegradable implant.

In one embodiment, the composition includes an effective amount of the biodegradable thermoplastic polymer; an effective amount of the biocompatible end-capped oligomeric liquid; and an effective amount of bioactive agent, and wherein the solid implant releases an effective amount of bioactive agent over time as the solid implant biodegrades in the patient and optionally the patient is a human.

In one embodiment, the composition further includes a biocompatible polar aprotic liquid including N-methyl-2-pyrrolidone, 2-pyrrolidone, N,N-dimethylformamide, dimethyl sulfoxide, propylene carbonate, caprolactam, triacetin, or a combination thereof.

In one embodiment, an implant is provided including: (a) a biocompatible thermoplastic polymer that is at least substantially insoluble in an aqueous medium or a body fluid; (b) a biocompatible end-capped oligomeric liquid, wherein the biocompatible end-capped oligomeric liquid is very slightly soluble to completely soluble in all proportions in body fluid and at least partially dissolves at least a portion of the thermoplastic polyester, and optionally the amount of biocompatible end-capped oligomeric liquid decreases over time; and (c) a bioactive agent, a metabolite, or a prodrug thereof, wherein the implant has a solid or gel monolithic structure.

In one embodiment, the implant has a solid or gelatinous matrix, and the matrix being a core surrounded by a skin. In one embodiment, the implant is solid and microporous.

In one embodiment, the core contains pores of diameters from about 1 to about 1000 microns, and optionally the skin contains pores of smaller diameters than those of the core pores, and optionally the skin pores are of a size such that the skin is functionally non-porous in comparison with the core.

DEFINITIONS

The words and phrases presented in this patent application have their ordinary meanings to one of skill in the art unless otherwise indicated. Such ordinary meanings can be obtained by reference to their use in the art and by reference to general and scientific dictionaries, for example, *Webster's New World Dictionary*, Simon & Schuster, New York, N.Y., 1995, *The American Heritage Dictionary of the English Language*, Houghton Mifflin, Boston Mass., 1981, *Hawley's Condensed Chemical Dictionary*, 14th edition, Wiley Europe, 2002, and *The Merck Index*, 11th Edition, Merck & Co., Rahway N.J. 1989.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise. Thus, for example, a reference to "a formulation" includes a plurality of such formulations, so that a formulation of compound X includes formulations of compound X.

As used herein, the term "acid chloride" refers to a compound of the formula Z—C(O)Cl, wherein Z is a $C_{1-12}$ alkyl group, a $C_{1-12}$ haloalkyl group, an alkoxy-substituted $C_{1-12}$ alkyl group, and an ($C_6$-$C_{20}$) aryl group.

As used herein, the terms "pharmaceutically acceptable salts" or "acceptable salts" refer to derivatives wherein the parent compound is modified by making acid or base salts thereof. Examples of acceptable salts include, but are not limited to, mineral or organic acid salts of basic residues such as amines; alkali or organic salts of acidic residues such as carboxylic acids; and the like. The acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Specifically, the acceptable salts can include those salts that naturally occur in vivo in a mammal.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

As used herein, the term "alkenyl" refers to a monoradical branched or unbranched partially unsaturated hydrocarbon chain (i.e., a carbon-carbon, $sp^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

As used herein, the term "alkynyl" refers to a monoradical branched or unbranched hydrocarbon chain, having a point of complete unsaturation (i.e., a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

As used herein, the term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

As used herein, the term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, the term "halo" refers to fluoro, chloro, bromo, and iodo. Similarly, the term "halogen" refers to fluorine, chlorine, bromine, and iodine.

As used herein, the term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

As used herein, the term "alkanoyl" or "alkylcarbonyl" refers to —C(=O)R, wherein R is an alkyl group as previously defined.

As used herein, the term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

As used herein, the term "alkoxycarbonyl" refers to —C(=O)OR (or "COOR"), wherein R is an alkyl group as previously defined.

As used herein, the term "amino" refers to —NH$_2$. The amino group can be optionally substituted as defined herein for the term "substituted". The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

As used herein, the term "alkadiyl" refers to alkane moiety that has two single bonds originating therefrom, for example, propane-1,2-diyl, butane-1,3-diyl, or hexane-1,4-diyl.

As used herein, the term "alkatriyl" refers to alkane moiety that has three single bonds originating therefrom, for example, propane-1,2,3-triyl, butane-1,2,3-triyl, or hexane-1,2,4-triyl.

As used herein, the term "ambient temperature" generally refer to temperatures falling within the range of about 10 to about 40 degrees Centigrade. Preferably, ambient temperature refers to temperatures falling within the range of about 18 to about 30 degrees Centigrade.

As used herein, the term "bioactive agent" refers to any drug, organic compound, substance, nutrient or biologically beneficial agent including proteins, peptides (including polypeptides and oligopeptides), hormones, vaccines, oligonucleotides, genes, nucleic acids, steroids, antibiotics, antibodies, viruses, live cells, and other chemotherapeutic or non-therapeutic agents without limitation.

As used herein, the term "biocompatible" refers to the material, substance, compound, molecule, polymer, or system to which it applies, which should not cause severe toxicity, severe adverse biological reaction, or lethality in an animal to which it is administered at reasonable doses and rates.

As used herein, the term "biodegradable" refers to the material, substance, compound, molecule, polymer, or system which is cleaved, oxidized, hydrolyzed, or otherwise broken down by hydrolytic, enzymatic, or another mammalian biological process for metabolism to chemical units that can be assimilated or eliminated by the mammalian body.

As used herein, the term "bioerodable" refers to the material, substance, compound, molecule, polymer, or system that is biodegraded or mechanically removed by a mammalian biological process so that new surface is exposed.

As used herein, the term "chain extended" refers to a material that is used to build the molecular weight of the polymer by reaction of the chain extender with the reactive functionality in the polymer, that is, to chain extend the polymer. A suitable chain extender is typically a low equivalent weight active hydrogen containing compound having about 2 or more active hydrogen groups per molecule. The active hydrogen groups can be, for example, hydroxy groups.

As used herein, the term "drug" refers to a chemical capable of administration to an organism which modifies or alters the organism's physiology. More preferably, as used herein, the term "drug" refers to any substance intended for use in the treatment or prevention of disease, particularly for humans. Drug includes synthetic and naturally occurring toxins and bioaffecting substances as well as recognized pharmaceuticals, such as those listed in *The Merck Index*, 14$^{th}$ Ed., Merck Research Laboratories, Whitehouse Station, N.J., 2006, *The Physicians Desk Reference*, 62$^{nd}$ edition, 2008, pages 101-201, Thomson Healthcare Inc., Montvale, N.J.; *Goodman and Gilman's The Pharmacological Basis of Therapeutics*, 8$^{th}$ Edition (1990), pages 84-1614 and 1655-1715; and *The United States Pharmacopeia, The National Formulary*, USP XXII NF XVII (1990), the compounds of these references being herein incorporated by reference.

As used herein, the term "effective amount" refers to an amount of bioactive agent, an acceptable salt thereof, a derivative thereof, or any combination of those useful to treat or prevent the underlying disorder or disease, or to treat the symptoms associated with the underlying disorder or disease in a host. Synergy, as described, for example, by Chou and Talalay, *Adv. Enzyme Regul.* 22, 27-55 (1984), occurs when the effect of bioactive agent, an acceptable salt thereof, or a derivative thereof when administered in combination is greater than the additive effect of the bioactive agent, acceptable salt thereof, or a derivative thereof when administered alone as a single agent. In general, a synergistic effect is most clearly demonstrated at suboptimal concentrations of the bioactive agent, an acceptable salt thereof, or derivative thereof. Synergy can be in terms of lower cytotoxicity, increased activity, or some other beneficial effect of the combination compared with the individual components.

As used herein, the phrase "in one embodiment" refers a particular feature, structure, or characteristic. However, every embodiment may not necessarily include the particular feature, structure, or characteristic. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, the term "end-capped" or 'end-capped group" refers to a group present on a terminus of a polymer.

As used herein, the term "flowable" refers to the ability of the "flowable" composition to be transported under pressure into the body of a patient. For example, the flowable composition can have a low viscosity like water, and be injected with the use of a syringe, beneath the skin of a patient. The flowable composition can alternatively have a high viscosity as in a gel and can be placed into a patient through a high pressure transport device such as a high pressure syringe, cannula, needle, and the like. The ability of the composition to be injected into a patient should typically depend upon the viscosity of the composition. The composition should therefore have a suitable viscosity ranging from low like water to high like a gel, such that the composition can be forced through the transport device (e.g., syringe) into the body of a patient.

As used herein, a "gel" refers to a substance having gelatinous, jelly-like, or colloidal properties. See, e.g., *Concise*

Chemical and Technical Dictionary, 4th Edition, Chemical Publishing Co., Inc., p. 567, New York, N.Y. (1986).

As used herein, the term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imine (C=NH), sulfinyl (SO) and sulfonyl ($SO_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As used herein, the terms "lactide" and "glycolide" refer to either the cyclic dimeric esters of lactate and glycolate respectively when referring to reagents used in preparation of PLG copolymers, or to those segments as incorporated ring-opened dimers in the formed PLG copolymer molecular chains. Thus, a statement about polymerization of lactide and glycolide refers to a polymerization reaction of the cyclic dimeric esters, whereas a statement about a lactide or glycolide residue within a copolymer molecular chain refers to that grouping of atoms, ring-opened, and incorporated into the copolymer chain. When a copolymer is formed by polymerization of lactide and glycolide, each incorporated lactide or glycolide residue includes a pair of lactate or glycolate monomeric units, respectively. It is understood that when a lactide and glycolide residue in a copolymer molecular chain is referred to, the terms mean double (dimeric) units of two lactate (L-L), or two glycolate (G-G), residues in the molecular chain, respectively, such as is believed to result from the polymerization of lactide and glycolide. When a lactate (L) or a glycolate (G) residue in a copolymer molecular chain is referred to, the terms mean single lactate (L) or glycolate (G) residues in the molecular chain, respectively, which can be within a lactide (L-L) or a glycolide (G-G) residue if the given lactate or glycolate is adjacent to another lactate or glycolate residue, respectively, regardless of the method used to prepare the copolymer molecular chain. As in most polymeric systems, this arrangement of residues is not all or none. Instead, the arrangement is a predominance. Thus, for the lactide and glycolide copolymers, a predominance of L-L and G-G residues will be present with some L and G (single) residues also present. The chemical reason underlying this characterization is the polymerization process. During polymerization, growing polymer chains are broken and reformed. This scission may split dimer residues and recombine single residues. For the lactate and glycolate copolymers, L and G (single) residues will be present on a statistical basis. This kind of polymer will have a relatively few sequences including repeats of dimer residues because of entropy factors.

As used herein, the terms "lactic acid," "lactate," or "lactide" refer to any and all chiral forms of the compounds are included within the terms. Thus, "lactic acid" includes D-lactic acid, L-lactic acid, DL-lactic acid, or any combination thereof; "lactide" includes DD-lactide, DL-lactide, LD-lactide, LL-lactide, or any combination thereof.

As used herein, the term "liquid" refers to a substance that undergoes continuous deformation under a shearing stress. See, e.g., Concise Chemical and Technical Dictionary, 4th Edition, Chemical Publishing Co., Inc., p. 707, New York, N.Y. (1986).

As used herein, the term "oligomeric" refers to a molecule consisting of only a few monomeric units (e.g., dimer, trimer, tetramer, pentamer, hexamer, and the like).

As used herein, the term "patient" refers to a warm-blooded animal, and preferably a mammal, such as, for example, a cat, dog, horse, cow, pig, mouse, rat or primate, including a human.

As used herein, the term "polymer" refers to a molecule of one or more repeating monomeric residue units covalently bonded together by one or more repeating chemical functional groups. The term includes all polymeric forms such as linear, branched, star, random, block, graft, and the like. It includes homopolymers formed from a single monomer, copolymer formed from two or more monomers, terpolymers formed from three or more polymers, and polymers formed from more than three monomers. Differing forms of a polymer may also have more than one repeating, covalently bonded functional group. The term may also refer to substantially linear polyesters, also referred to herein as "PLG copolymers," predominantly formed of monomeric lactate and glycolate hydroxyacids, or lactide and glycolide dimeric hydroxyacids, and include compositions referred to in the art as poly(lactate-glycolate), poly(lactate(co)glycolate), poly (lactide-glycolide), poly(lactide (co)glycolide), PLG, PLGH, and the like, with the understanding that additional moieties may be included, such as core/initiator groups (for example, diols, hydroxyacids, and the like), capping groups (for example, esters of terminal carboxyl groups, and the like) and other pendant groups or chain extension groups covalently linked to or within a polyester backbone, including groups that cross-link the substantially linear polyester molecular chains, without departing from the meaning assigned herein. PLG copolymers, as the term is used herein, includes molecular chains with terminal hydroxyl groups, terminal carboxyl groups (i.e., acid-terminated, sometimes termed PLGH) and terminal ester groups (i.e., capped).

As used herein, the term "polyester" refers to polymers containing monomeric repeats, at least in part, of the linking group: —OC(=O)— or —C(=O)O—.

As used herein, the terms "skin" and "core" of a skin and core matrix mean that a cross section of the matrix should present a discernable delineation between an outer surface and the inner portion of the matrix. The outer surface is the skin and the inner portion is the core.

As used herein, the term "solvent" refers to a liquid, usually organic, that serves to dissolve a polymer material to provide a homogeneous solution of the polymer material.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X', —R, —O⁻, —OR, —SR, —S⁻, —NR₂, —NR₃, =NR, —CX'₃, —CN, —OCN, —SCN, —N=C=O, —NCS, —NO, —NO₂, =N₂, —N₃, NC(=O) R, —C(=O)R, —C(=O)NRR—S(=O)₂O⁻, —S(=O)₂ OH, —S(=O)₂R, —OS(=O)₂OR, —S(=O)₂NR, —S(=O)R, —OP(=O)O₂RR, —P(=O)O₂RR—P(=O) (O⁻)₂, —P(=O)(OH)₂, —C(=O)R, —C(=O)X', —C(S)R, —C(O)OR, —C(O)O⁻, —C(S)OR, —C(O)SR, —C(S)SR, —C(O)NRR, —C(S)NRR, —C(NR)NRR, where each X' is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

As used herein, the term "thermoplastic" as applied to a polymer refers to the polymer repeatedly should melt upon heating and should solidify upon cooling. It signifies that no or a slight degree of cross-linking between polymer molecules is present. It is to be contrasted with the term "thermoset," which indicates that the polymer should set or substantially cross-link upon heating or upon application of a similar reactive process and should no longer undergo melt-solidification cycles upon heating and cooling.

As used herein, the terms "treating," "treat," or "treatment" includes (i) preventing a pathologic condition (e.g., schizophrenia) from occurring (e.g., prophylaxis); (ii) inhibiting the pathologic condition (e.g., schizophrenia) or arresting its development; and (iii) relieving the pathologic condition (e.g., relieving the symptoms associated with schizophrenia).

DESCRIPTION OF THE INVENTION

The present invention provides biocompatible oligomer-polymer compositions for the in situ formation of implants, wherein the implants release a bioactive agent, a metabolite, or a prodrug thereof, at a controlled rate. These compositions include biocompatible end-capped oligomeric liquids that are useful for forming implants in situ because they have very good biocompatibility and low toxicity. These biocompatible end-capped oligomeric liquids are effective for dissolving a specific polymer, have some degree of water solubility, and can be custom tailored to dissolve a particular active pharmaceutical ingredient. By being end-capped oligomers of, for example, lactide, glycolide, lactic acid, and/or glycolic acid, these biocompatible oligomeric liquids are readily degraded by the body through hydrolysis to yield compounds with known and acceptable toxicological characteristics.

The biocompatible end-capped oligomeric liquids prepared herein are especially advantageous in preparing single syringe ATRIGEL® formulations because they are not reactive with the polymer and/or the drug and will inhibit water from entering the ATRIGEL® formulation. The biocompatible end-capped oligomeric liquids have similar chemical structures as the implant polymer and will react with any water that may be present in the formulation and thereby increase the storage life of the ATRIGEL® product. Further, unlike the biocompatible end-capped oligomeric liquids disclosed by Voelkel et al. in U.S. Pat. No. 6,815,469, which possess free carboxyl and free hydroxyl groups that may react with the implant polymer, the biocompatible end-capped oligomeric liquids described herein are more hydrophobic and offer better solubility and stability for the implant polymer.

In one embodiment, a flowable composition is provided including: (a) a biodegradable thermoplastic polymer that is at least substantially insoluble in body fluid; (b) a biocompatible end-capped oligomeric liquid; and (c) a bioactive agent, a metabolite, or a prodrug thereof.

Biocompatible End-Capped Oligomeric Liquids

The biocompatible end-capped oligomeric liquid is of the formula I, II, III, IV, or V:

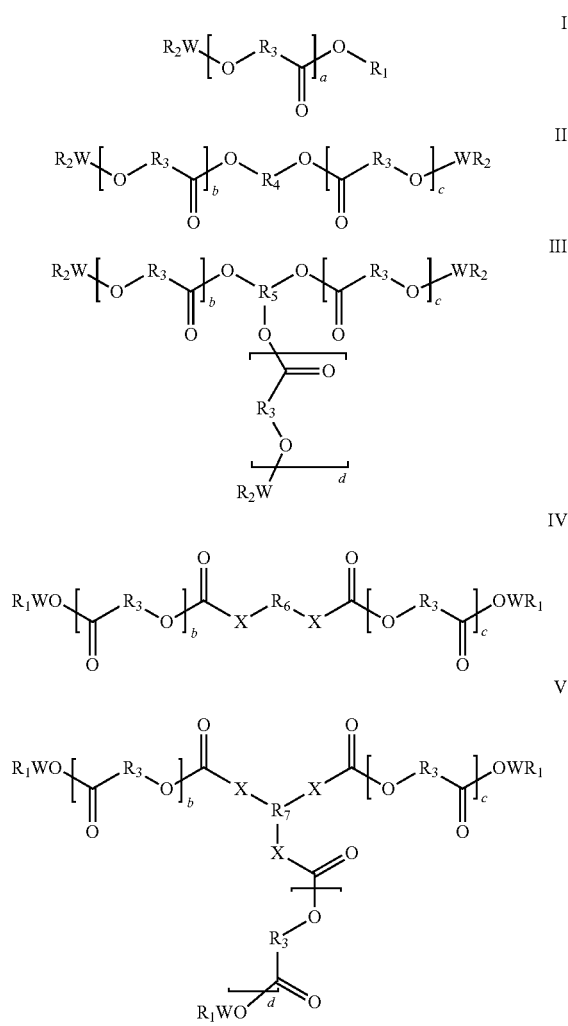

wherein:
each $R_1$ is independently hydrogen, $(C_1-C_{12})$alkyl, or $(C_1-C_{12})$alkylenecarboxylic$(C_1-C_{12})$alkylester;
each $R_2$ is independently hydrogen, $(C_1-C_{12})$alkyl, carbonyl$(C_1-C_{12})$alkyl, carboxylic$(C_1-C_{12})$alkylester, or carboxylic$(C_1-C_{12})$alkylester, wherein $R_2$ in not hydrogen in Formula I if W is absent, and further wherein at least one $R_2$ is not hydrogen in Formulas II and III if W is absent;
each $R_3$ is independently $(C_1-C_{12})$alkylene;
$R_4$ is $(C_1-C_{12})$alkylene, carbonyl$(C_1-C_{12})$alkylcarbonyl, or $(C_3-C_{12})$cycloalkadiyl;
$R_5$ is $(C_1-C_{12})$alkatriyl or $(C_3-C_{12})$cycloalkatriyl;
$R_6$ is $(C_1-C_{12})$alkylene, $(C_1-C_{12})$alkyne, $(C_3-C_{12})$cycloalkadiyl, $(C_1-C_{12})$alkatriyl, or $(C_3-C_{12})$cycloalkatriyl;
$R_7$ is $(C_1-C_{12})$alkylene or $(C_1-C_{12})$alkatriyl,
X is absent or oxygen;
W is absent, carbonyl, carbonyloxy, or oxycarbonyl; and
any alkyl or alkylene of $R_1$, $R_2$, $R_3$, $R_4$, $R_5$, $R_6$ and $R_7$ can optionally be substituted on carbon with one or more oxo, hydroxy, halogen, nitro, cyano, ($C_1$-$C_{12}$)alkyl, ($C_1$-$C_6$)alkoxy, trifluoromethyl, and optionally interrupted on carbon with one or more oxy, imino, or thio, and is optionally partially unsaturated; and each a, b, c, and d is independently 0, 1, 2, 3, 4, or 5.

In one embodiment, each $R_1$ is independently hydrogen, —$(CH_2)_mCH_3$, —$CH_2CH_2(OCH_2CH_2)_mO(CH_2)_nCH_3$, —$CH_2CH_2(OCH_2CH_2)_mOCOCH_3$, —$CH_2COOY$, —$CH(CH_3)COOY$, —$CH_2CH_2COOY$, —$CH_2CH_2CH_2COOY$, —$CH_2CH_2CH_2CH_2COOY$, —$CH_2CH_2CH_2CH_2CH_2COOY$, —$CH_2CH(CH_3)Y$, or -(cyclo$C_6H_{11}$)—, wherein each m and n is independently 0, 1, 2, 3, 4, 5, 6, or 7;

each $R_2$ is independently hydrogen, —$CH_3$, —$CH_2CH_3$, —$(CH_2)_oCH_3$, —$CH_2CH_2(OCH_2CH_2)_oOCH_3$, —$CH_2CH_2(OCH_2CH_2)_oOCH_2CH_3$, —$CH_2CH_2(OCH_2CH_2)_oOCOCH_3$, —$COCH_3$, —$CO(CH_2)_oCH_3$, —$COO(CH_2)_oCH_3$, or —$CO(OCH_2CH_2)_oCH_3$, wherein o is 0, 1, 2, 3, 4, 5, 6, or 7, wherein $R_2$ in not hydrogen in Formula I if W is absent, and further wherein at least one $R_2$ is not hydrogen in Formulas II and III if W is absent;

each $R_3$ is independently —$(CH_2)_p$—, —$CH(CH_3)$—, —$(CH_2CH_2O)_pCH_2$—, —$(CH(CH_3)CH_2)$—, or —$(CH(CH_2CH_3)CH_2)$—, wherein p is 0, 1, 2, 3, 4, 5, 6, or 7, $R_4$ is —$(CH_2)_q$—, —$CO(CH_2)_qCO$—, —$(CH_2CH_2O)_qCH_2CH_2$—, —$CH_2CH_2CH_2CH_2CH_2CH_2$—, —$(CH_2)_qCH(CH_3)$—, —$((CH_2)_qO)_q$—, —$CH_2CH(Y)CH_2$—, cyclohexane-1,2-diyl, cyclohexane-1,3-diyl or cyclohexane-1,4-diyl, wherein q is 1, 2, 3, 4, 5, 6, or 7;

$R_5$ is (—$CH_2)_2CH$—, (—$CH_2)_3CCH_3$, (—$CH_2)_3CCH_2CH_3$, or 1,2,6-hexanetriyl;

$R_6$ is —$CH=CH$—, —$(CH_2)_r$—, —$O(CH_2CH_2O)_r$— wherein r is 1, 2, 3, 4, 5, 6, or 7;

$R_7$ is (—$CH_2)_2CH$—, (—$CH_2)_2COH$—, (—$CH_2)(—CHOH)CH$—, (—$CH_2)(—CO)CH$—, or (—$CH_2)(—CH=)C$—;

X is absent or oxygen;

W is absent, —CO—, —COO—, or —OCO—; and

Y is —$CH_3$, —$C_2H_5$, —$C_3H_7$, or —$C_4H_9$.

In one embodiment, each $R_1$ is independently hydrogen, —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$CH_2CH_2(OCH_2CH_2)_2OCH_3$, —$CH_2CH_2(OCH_2CH_2)_2OCH_2CH_3$, or —$CH_2CH_2(OCH_2CH_2)_2OCOCH_3$;

each $R_2$ is independently hydrogen, —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$CH_2CH_2(OCH_2CH_2)_2OCH_3$, —$CH_2CH_2(OCH_2CH_2)_2OCH_2CH_3$, or —$CH_2CH_2(OCH_2CH_2)_2OCOCH_3$, wherein $R_2$ in not hydrogen in Formula I if W is absent, and further wherein at least one $R_2$ is not hydrogen in Formulas II and III if W is absent;

each $R_3$ is independently —$CH_2$—, —$(CH_2)_2$—, —$(CH_2)_3$—, —$(CH_2)_4$—, —$(CH_2)_5$—, —$(CH_2)_6$—, —$(CH_2)_7$—, —$CH(CH_3)$—, —$(CH(CH_3)CH_2)$—, —$(CH(CH_2CH_3)CH_2)$—, or

—$(CH_2CH_2OCH_2)$—;

$R_4$ is —$(CH_2)_3$—, —$(CH_2)_4$—, —$(CH_2)_5$—, —$(CH_2)_6$—, —$COCH_2CO$—, —$CO(CH_2)_2CO$—, —$CO(CH_2)_3CO$—, —$CO(CH_2)_4CO$—, —$CO(CH_2)_5CO$—, —$CO(CH_2)_6CO$—, —$CO(CH_2)_7CO$—, —$CO(CH_2)_8CO$—, —$(CH_2CH_2O)_2CH_2CH_2$—, —$(CH_2CH_2O)_3CH_2CH_2$—, —$(CH_2CH_2O)_4CH_2CH_2$—, —$(CH_2CH_2O)_5CH_2CH_2$—, —$(CH_2CH_2O)_6CH_2CH_2$—, or —$CH_2CH_2CH_2CH_2CH_2CH_2$—;

$R_5$ is (—$CH_2)_2CH$—;

$R_6$ is —$CH=CH$—, —$(CH_2)$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$O(CH_2CH_2O)$—, —$O(CH_2CH_2O)_2$—, —$O(CH_2CH_2O)_3$—, —$O(CH_2CH_2O)_4$—, —$O(CH_2CH_2O)_5$—, or —$O(CH_2CH_2O)_6$—;

$R_7$ is (—$CH_2)_2CH$—, (—$CH_2)_2COH$—, (—$CH_2)(—CHOH)CH$—, (—$CH_2)(—CO)CH$—, or (—$CH_2)(—CH=)C$—;

X is absent or oxygen;

W is absent, —CO—, —COO—, or —OCO—; and each a, b, c, and d is independently 0, 1, 2, 3, or 4.

Exemplary synthetic routes to the biocompatible end-capped oligomeric liquids in formulas I, II, III, IV, and V are illustrated in schemes 1-14.

The compositions described herein can be prepared by any of the applicable techniques of organic synthesis and polymer chemistry. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis: Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); *Comprehensive Organic Transformations*, 2nd Edition, Larock, R. C., John Wiley & Sons, New York (1999), *Textbook of Polymer Chemistry*, $3^{rd}$ Edition, Fred W. Billmeyer, John Wiley & Sons, New York (1984), *Organic Polymer Chemistry*, $2^{nd}$ Edition, K. J. Saunders, Chapman and Hall, New York (1973), and *Polymer Science*, V. R. Gowariker et al., John Wiley & Sons, New York (1986).

Scheme 1

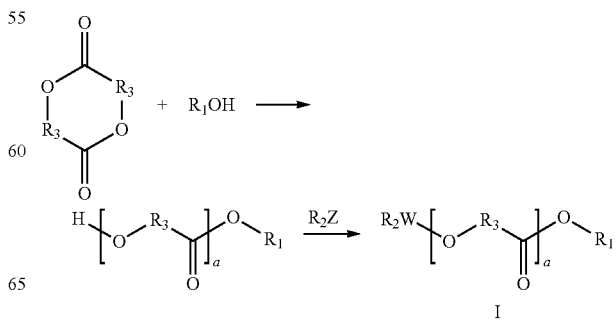

Scheme 2
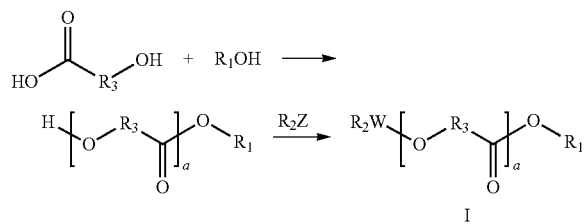
Scheme 3
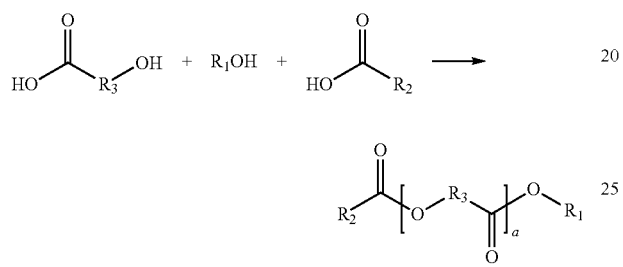
Scheme 4
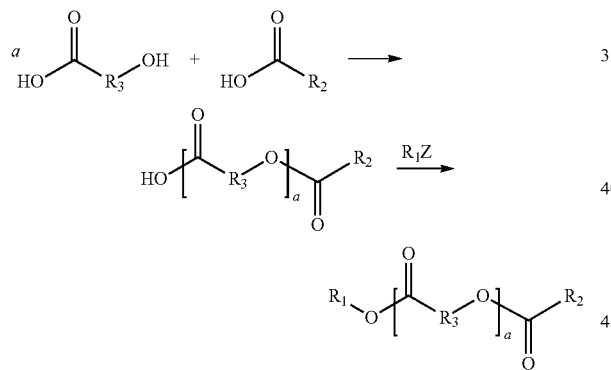
Scheme 5
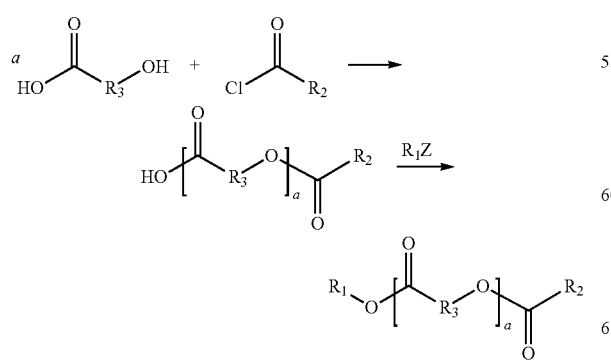
Scheme 6
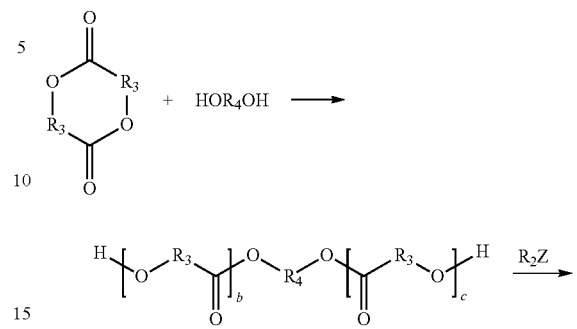
Scheme 7
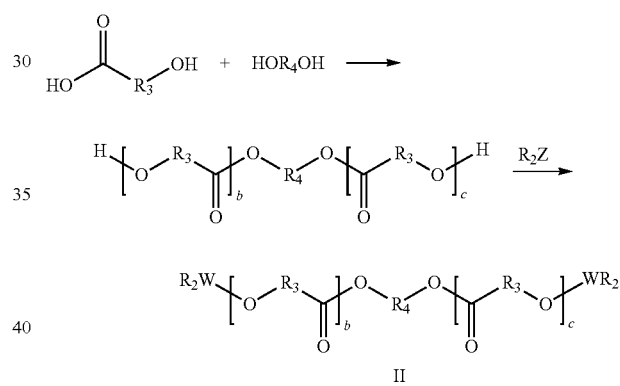
Scheme 8
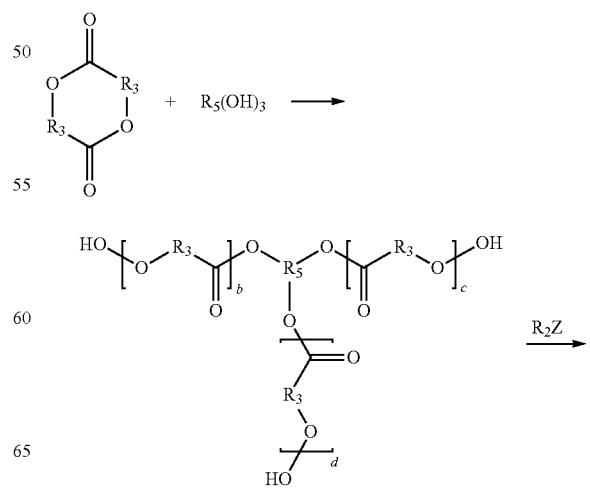

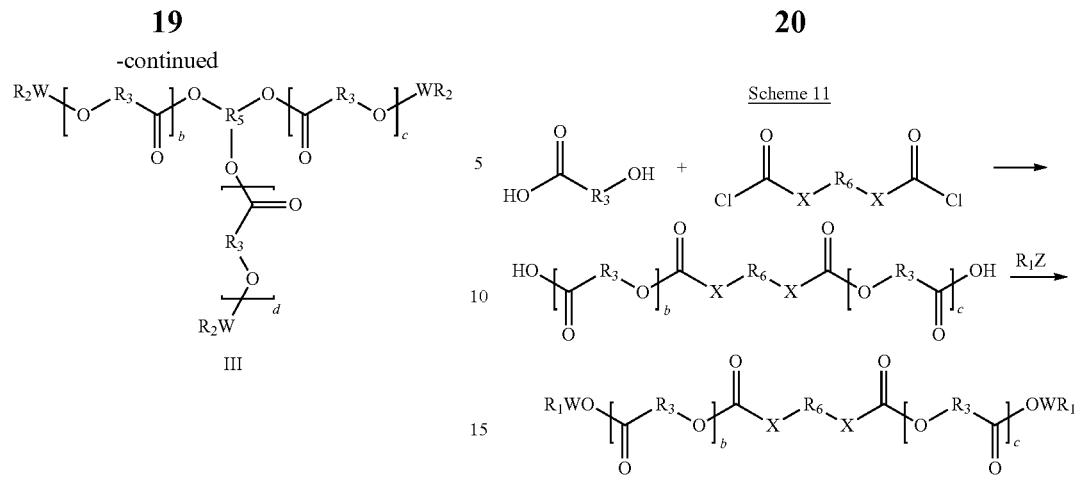
Scheme 9
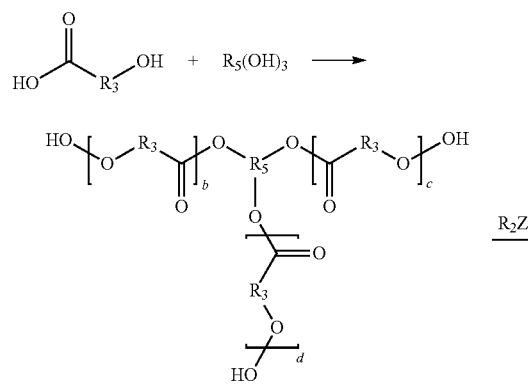
Scheme 10
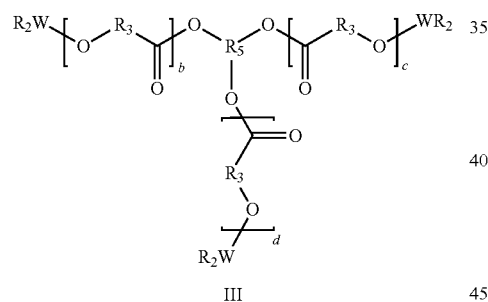
Scheme 11
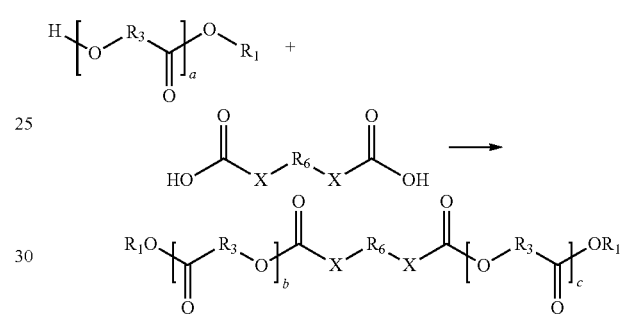
Scheme 12
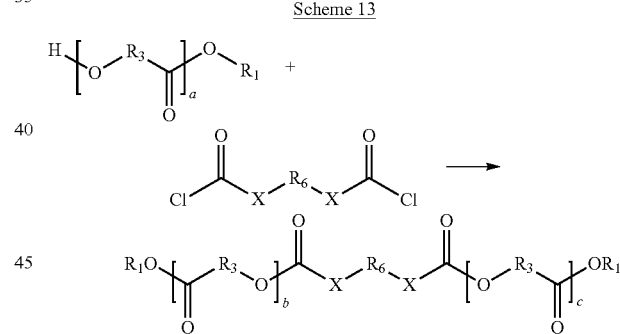
Scheme 13
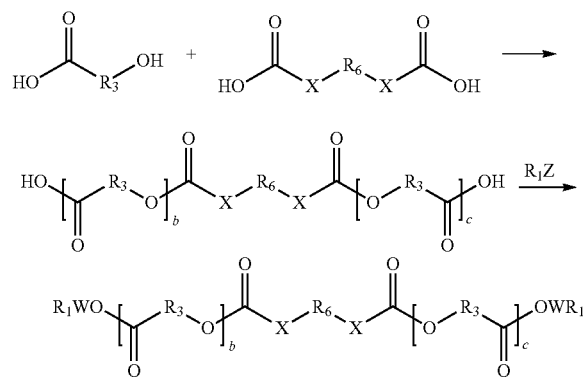
Scheme 14
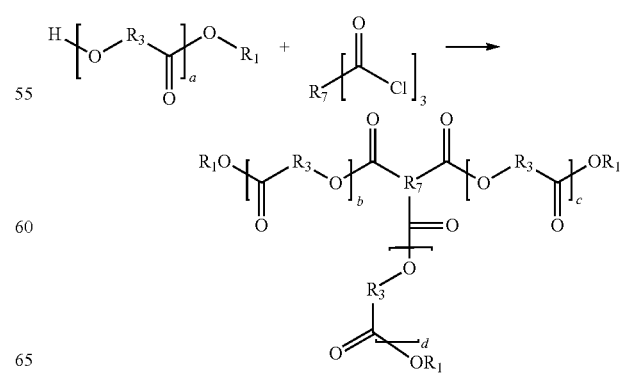

In Schemes 1-14, each $R_1Z$ may be independently, for example, $R_1OH$, $R_1I$ (wherein I is halogen), $R_1N_2$, $R_1COCl$, $R_1COOH$, $R_1COOCOR_1$, $R_1COOCH_3$, and the like, and each $R_2Z$ may be independently, for example, $R_2OH$, $R_2I$ (wherein I is halogen), $R_2N_2$, $R_2COCl$, $R_2COOH$, $R_2COOCOR_2$, $R_2COOCH_3$, and the like.

The intermediates in Scheme 1 are routinely prepared using the methods developed by, for example, Claborn, U.S. Pat. No. 2,371,281, Zeile et al., German Patent No. DE 1020312, and Rehberg et al., *J. Amer. Chem. Soc.*, 74, 1609, (1952), or by the enzymatic methods developed by, for example, Jeon et al. *Tetrahedron Letters*, 47, 6517-6520 (2006).

Suitable $C_2$ to $C_{10}$ lactones may include, for example, glycolide ($R_3$ is $CH_2$), lactide ($R_3$ is $CHCH_3$), p-dioxanone, ε-caprolactone, and the like, or combinations thereof.

Suitable $C_2$ to $C_{10}$ hydroxycarboxylic acids may include, for example, 2-hydroxyethanoic acid, 2-hydroxyacetic acid, 2-hydroxypropanoic acid, 2-hydroxybutyric acid, 2-hydroxyvaleric acid, 2-hydroxyhexanoic acid, 2-hydroxyheptanoic acid, 2-hydroxyoctanoic acid, 2-hydroxy-2-methylpropanoic acid, 2-hydroxy-2-methylbutyric acid, 2-hydroxy-2-ethylbutyric acid, 2-hydroxy-2-methylvaleric acid, 2-hydroxy-2-ethylvaleric acid, 2-hydroxy-2-propylvaleric acid, 2-hydroxy-2-butylvaleric acid, 2-hydroxy-2-methylhexanoic acid, 2-hydroxy-2-ethylhexanoic acid, 2-hydroxy-2-propylhexanoic acid, 2-hydroxy-2-butylhexanoic acid, 2-hydroxy-2-pentylhexanoic acid, 2-hydroxy-2-methylheptanoic acid, 2-hydroxy-2-ethylheptanoic acid, 2-hydroxy-2-methyloctanoic acid, 2-hydroxy-2-ethyloctanoic acid, 3-hydroxypropanoic acid, 3-hydroxybutanoic acid, 3-hydroxypentanoic acid, 3-hydroxyhexanoic acid, 3-hydroxyheptanoic acid, 3-hydroxyoctanoic acid, 3-hydroxy-3-methylbutanoic acid, 3-hydroxy-3-methylpentanoic acid, 3-hydroxy-3-ethylpentanoic acid, 3-hydroxy-3-methylhexanoic acid, 3-hydroxy-3-ethylhexanoic acid, 3-hydroxy-3-propylhexanoic acid, 3-hydroxy-3-methylheptanoic acid, 3-hydroxy-3-ethylheptanoic acid, 3-hydroxy-3-propylheptanoic acid, and the like, or combinations thereof.

Suitable $C_1$ to $C_{12}$ alcohols may include, for example, mono-alcohols, diol, triols, and other polyols.

Suitable $C_1$ to $C_{12}$ mono-alcohols may include, for example, methanol, ethanol, n-propanol, isopropanol, n-butanol, n-hexanol, n-heptanol, n-octanol, s-butanol, allyl alcohol, 2-butoxyethyl, 2-(2-butoxyethoxy)ethanol, and the like, or combinations thereof.

Suitable $C_2$ to $C_{10}$ diols or glycols may include, for example, ethylene glycol, 1,4-cyclohexanedimethanol, diethylene glycol, triethylene glycol, propane-1,3-diol, butane-1,4-diol, pentane-1,5-diol, hexane-1,6-diol, 3-methylpentane-2,4-diol, 2-methylpentane-1,4-diol, 2,2,4-trimethylpentane-1,3-diol, 2-ethylhexane-1,3-diol, 2,2-diethylpropane-1,3-diol, hexane-1,3-diol, and the like, or combinations thereof.

Suitable $C_3$ to $C_{12}$ polyols, may include, for example, trimethylolpropane, pentaerythritol, glycerol, trimellitic anhydride, trimethylolpropane, pyromellitic dianhydride, pentaerythritol, and the like, or combinations thereof.

Suitable oligomeric intermediates include, for example, ethyl lactyllactate, ethyl glycoloyloxyacetate, 2-hydroxyethyl lactyllactate, n-propyl lactyllactate, 2-hydroxypropyl lactyl lactate, 1-methyl-2-hydroxypropyl lactyllactate, n-butyl lactyllacetate, s-butyl lactyllacetate, n-hexyl lactyllacetate, n-octyl lactyllacetate, 2-octyl lactyllacetate, allyl lactyllacetate, 2-butoxyethyl lactyllacetate, 2-(2-butoxyethoxyethoxy)ethyl lactyllacetate, tetrahydrofurfuryl lactyllacetate, 2-chloroethyl, and the like, or combinations thereof.

Suitable $C_3$ to $C_{12}$ dicarboxylic acids may include, for example, oxalic acid, malonic acid, gulutaric acid, succinic acid, adipic acid, pimelic acid, suberic acid, azelaic acid, sebacic acid, undecanedicarboxylic acid, dodecanedicarboxylic acid, 1,4-cyclohexanedicarboxylic acid, and the like, or combinations thereof.

Suitable $C_3$ to $C_{12}$ tricarboxylic acids may include, for example, propanetricarboxylic acid, trimellitic acid, pyromellitic acid, 1,3,6-hexanetricarboxylic acid, and the like, or combinations thereof.

Suitable activated carbonyl compounds may include, for example, acid chlorides, anhydrides, and the like.

Suitable acid chlorides, may include, for example, acetyl chloride, butyryl chloride, pentanoyl chloride, hexanoyl chloride, 2-methylbutyryl chloride, furoyl chloride, and the like, or combinations thereof.

In one embodiment, the bioactive agent, a metabolite, or a prodrug thereof, is filled into a syringe, the syringe is sealed, and the entire drug substance syringe is terminally sterilized by gamma irradiation. The biodegradable polymer is dissolved in a biocompatible end-capped oligomeric liquid and filled in a second syringe. The syringe is sealed and the delivery system is terminally sterilized by gamma irradiation. At the time of injection, the syringes are coupled through the luer-lock connection and the product is constituted by cycling the components between the two syringes. In this way, the drug is incorporated into the delivery system and very little is lost to the device.

In another embodiment, the bioactive agent, a metabolite, or a prodrug thereof, the biodegradable polymer, and the biocompatible end-capped oligomeric liquid is added to a syringe and shaken to dissolve the bioactive agent, a metabolite, or a prodrug thereof, and the biodegradable polymer. The syringe is sealed, the delivery system is terminally sterilized by gamma irradiation, and the product is ready for shipment and use.

The flowable composition is a combination of a biodegradable substantially water-insoluble thermoplastic polymer, a biocompatible end-capped oligomeric liquid, and a bioactive agent, a metabolite, or a prodrug thereof. The biocompatible end-capped oligomeric liquid has a solubility in body fluid ranging from practically insoluble to completely soluble in all proportions. The biodegradable thermoplastic polymer may be a homopolymer, a copolymer or a terpolymer of repeating monomeric units linked by such groups as ester groups, anhydride groups, carbonate groups, amide groups, urethane groups, urea groups, ether groups, esteramide groups, acetal groups, ketal groups, orthocarbonate groups and any other organic functional group that can be hydrolyzed by enzymatic or hydrolytic reaction (i.e., is biodegradable by hydrolytic action). The preferred thermoplastic polymer, polyester, may be composed of units of one or more hydroxycarboxylic acid residues or diol and dicarboxylic acid residues, wherein the distribution of differing residues may be random, block, paired or sequential. The thermoplastic polymer is preferably a thermoplastic polyester of one or more $C_2$ to $C_{10}$ hydroxycarboxylic acids or one or more $C_2$ to $C_{12}$ diols and dicarboxylic acids. Especially preferably, the thermoplastic polymer is a polyester of one or more hydroxyl carboxyl dimers, for example, lactide, glycolide, and the like.

The specific and preferred biodegradable thermoplastic polymers and biocompatible end-capped oligomeric liquids; the concentrations of thermoplastic polymers, biocompatible end-capped oligomeric liquids, the bioactive agents, metabolites, or prodrugs thereof; the molecular weights of the thermoplastic polymer; and the weight or mole ranges of components of the solid implant described herein are exemplary.

They do not exclude other biodegradable thermoplastic polymers and biocompatible end-capped oligomeric liquids; other concentrations of thermoplastic polymers, biocompatible end-capped oligomeric liquids, bioactive agents; other molecular weights of the thermoplastic polymer; and other components within the solid implant.

One embodiment provides a flowable composition suitable for use in providing a controlled sustained release implant, a method for forming the flowable composition, a method for using the flowable composition, the biodegradable sustained release solid or gel implant that is formed from the flowable composition, a method of forming the biodegradable implant in situ, a method for treating disease through use of the biodegradable implant and a kit that includes the flowable composition. The flowable composition may preferably be used to provide a biodegradable or bioerodible microporous in situ formed implant in animals.

The flowable composition is composed of a biodegradable thermoplastic polymer in combination with a biocompatible end-capped oligomeric liquid and a bioactive agent, a metabolite, or a prodrug thereof. The biodegradable thermoplastic polymer is substantially insoluble in aqueous medium and/or in body fluid, biocompatible, biodegradable, and/or bioerodible within the body of a patient. The flowable composition may be administered as a liquid or gel into tissue and forms an implant in situ. Alternatively, the implant may be formed ex vivo by combining the flowable composition with an aqueous medium. In this embodiment, the preformed implant may be surgically administered to the patient. In either embodiment, the thermoplastic polymer coagulates or solidifies to form the solid or gel implant upon the dissipation, dispersement, or leaching of the biocompatible end-capped oligomeric liquid from the flowable composition when the flowable composition contacts a body fluid, an aqueous medium, or water. The coagulation or solidification entangles and entraps the other components of the flowable composition, for example, the bioactive agent, a metabolite, or a prodrug thereof, excipients, organic substances, and the like, so that they become dispersed within the gelled or solidified implant matrix. The flowable composition is biocompatible and the polymer matrix of the implant does not cause substantial tissue irritation or necrosis at the implant site. The implant delivers a sustained level of the bioactive agent, a metabolite, or a prodrug thereof, to the patient. Preferably, the flowable composition can be a liquid or a gel, suitable for injection in a patient (e.g., human).

One embodiment surprisingly improves the bioavailability of a sustained release formulation of the bioactive agent, a metabolite, or a prodrug thereof. In addition, this embodiment provides: (a) relatively low volume injections; (b) improved local tissue tolerance at the injection site; (c) an opportunity to use a subcutaneous injection rather than an intramuscular injection; and (d) less frequent injections compared to other products.

By comparison to formulations derived from other sustained release drug delivery technologies, the bioactive agent, a metabolite, or a prodrug thereof, sustained release delivery system should provide: (a) superior release kinetics with minimal burst; (b) increased duration of drug release with less frequent injections; (c) markedly improved bioavailability; (d) improved local tissue tolerance due to a small injection volume, and (e) the ability to use of a subcutaneous injection rather than intramuscular injection. Taken together, these features make a highly beneficial bioactive agent sustained release delivery system.

The biocompatible end-capped oligomeric liquids suitable for use in the flowable compositions display a range of solubilities in aqueous medium, body fluid, or water. That range includes complete insolubility at all concentrations upon initial contact, to complete solubility at all concentrations upon initial contact between the biocompatible end-capped oligomeric liquid and the aqueous medium, body fluid, or water.

While the solubility or insolubility of the biocompatible end-capped oligomeric liquid in water can be used as a solubility guide, its water solubility or insolubility in body fluid typically should vary from its solubility or insolubility in water. Relative to water, body fluid contains physiologic salts, lipids, proteins, and the like, and should have a differing solvating ability for oligomeric liquids. This phenomenon is similar to the classic "salting out" characteristic displayed by saline relative to water. Body fluid displays similar variability relative to water but in contrast to a "salting out" factor, body fluid typically has higher solvating ability for most oligomeric liquids than does water. This higher ability is due in part to the greater lipophilic character of body fluid relative to water, and also in part to the dynamic character of body fluid. In a living organism, body fluid is not static but rather moves throughout the organism. In addition, body fluid is purged or cleansed by tissues of the organism so that body fluid contents are removed. As a result, body fluid in living tissue should remove, solvate, or dissipate oligomeric liquids that are utterly insoluble in water.

Pursuant to the foregoing understanding of the solubility differences among water, aqueous media, and body fluid, the biocompatible end-capped oligomeric liquid used may be completely insoluble to completely soluble in water when the two are initially combined. Preferably the biocompatible end-capped oligomeric liquid is slightly soluble in water. The corresponding solubilities of the biocompatible end-capped oligomeric liquids in aqueous media and body fluid should tend to track the trends indicated by the water solubilities. In body fluid, the solubilities of the biocompatible end-capped oligomeric liquids should tend to be higher than those in water.

When a biocompatible end-capped oligomeric liquid that is insoluble to slightly soluble in body fluid is used in any of the embodiments of the sustained release delivery system, it should allow water to permeate into the implanted delivery system over a period of time ranging from seconds to weeks or months. This process may decrease or increase the delivery rate of the bioactive agent, a metabolite, or a prodrug thereof, and in the case of the flowable composition, it should affect the rate of coagulation or solidification. When a biocompatible end-capped oligomeric liquid that is moderately soluble to very soluble in body fluid is used in any of the embodiments of the delivery system, it should diffuse into body fluid over a period of minutes to days. The diffusion rate may decrease or increase the delivery rate of the bioactive agent, a metabolite, or a prodrug thereof. When highly soluble oligomeric liquids are used, they should diffuse from the delivery system over a period of seconds to hours. Under some circumstances, this rapid diffusion is responsible at least in part for the so-called burst effect. The burst effect, is a short-lived but rapid release of bioactive agent upon implantation of the delivery system followed by a long-lived, slow release of bioactive agent.

The type and amount of biocompatible oligomeric present in the flowable composition should typically depend on the desired properties of the controlled release implant as described in detail below. Preferably, the flowable composition includes about 10 wt. % to about 90 wt. % or more preferably about 3 wt. % to about 70 wt. % of a biocompatible end-capped oligomeric liquid.

The solubility of the biodegradable thermoplastic polymers in the various biocompatible end-capped oligomeric liquids should differ depending upon their crystallinity, their hydrophilicity, hydrogen-bonding, and molecular weight. Lower molecular-weight polymers should normally dissolve more readily in the biocompatible end-capped oligomeric liquids than high-molecular-weight polymers. As a result, the concentration of a thermoplastic polymer dissolved in the various biocompatible end-capped oligomeric liquids should differ depending upon type of polymer and its molecular weight. Moreover, the higher molecular-weight thermoplastic polymers should tend to give higher solution viscosities than the low-molecular-weight materials.

When the biocompatible end-capped oligomeric liquid forms part of the flowable composition, it functions to enable easy, non-surgical placement of the sustained release delivery system into living tissue. It also facilitates transformation of the flowable composition to an in situ formed implant. Although it is not meant as a limitation of the invention, it is believed that the transformation of the flowable composition is the result of the dissipation of the biocompatible end-capped oligomeric liquid from the flowable composition into the surrounding body fluid and tissue and the infusion of body fluid from the surrounding tissue into the flowable composition. It is believed that during this transformation, the thermoplastic polymer and biocompatible end-capped oligomeric liquid within the flowable composition partition into regions rich and poor in polymer.

For the flowable compositions, the concentration of the thermoplastic polymer in the biocompatible end-capped oligomeric liquid should range from about 0.01 g per mL of biocompatible end-capped oligomeric liquid to a saturated concentration. Typically, the saturated concentration should be in the range of 80 to 95 wt. % solids or about 4 gm per mL to about 5 gm per mL of biocompatible end-capped oligomeric liquid, assuming that the biocompatible end-capped oligomeric liquid weighs approximately 1 gm per mL.

For polymers that tend to coagulate slowly, a solvent mixture can be used to increase the coagulation rate. In essence, one liquid component of the solvent mixture is a good solvent for the polymer, and the other liquid component of the solvent mixture is a poorer solvent or a non-solvent. The two liquids are mixed at a ratio such that the polymer is still soluble but precipitates with the slightest increase in the amount of non-solvent, for example, water in a physiological environment. By necessity, the solvent system should be miscible with both the polymer and water.

For the formed implants, the presence of the biocompatible end-capped oligomeric liquid can serve to provide the following properties: plasticization, moldability, flexibility, increased or decreased homogeneity, increased or decreased release rate for the bioactive agent, a metabolite, or a prodrug thereof, leaching, promotion or retardation of body fluid influx into the implant, patient comfort, compatibility of thermoplastic polymer and bioactive agent, and the like. Generally the concentration of biocompatible end-capped oligomeric liquid in the formed implant may range from about 0.001 wt. % to as much as about 30 wt. %. Generally, the concentration should be less than an amount that would cause reversion of the formed implant into a flowable composition. Also, the biocompatible end-capped oligomeric liquid may preferentially be chosen so as to display less than substantial ability to dissolve the thermoplastic polymer.

The pliability of the implant can be substantially maintained throughout its life if additives, for example, the biocompatible end-capped oligomeric liquid are maintained in the implant. Such additives also can act as a plasticizer for the thermoplastic polymer and at least in part may remain in the implant. One such additive having these properties is a biocompatible end-capped oligomeric liquid of low water solubility to water insolubility. Such a biocompatible end-capped oligomeric liquid providing these pliability and plasticizing properties may be included in the delivery system as the sole biocompatible end-capped oligomeric liquid or may be included in addition to a biocompatible end-capped oligomeric liquid that is moderately to highly water soluble.

Biocompatible end-capped oligomeric liquids of low water solubility or water insolubility, for example, those forming aqueous solutions of no more than 5% by weight in water, can function as a pliability, plasticizing component, and in addition can act as the solvating component for the flowable compositions. Such biocompatible end-capped oligomeric liquids can act as plasticizers for the thermoplastic polymer. When the biocompatible end-capped oligomeric liquid has these properties, it is a member of a subgroup of oligomeric liquids termed "plasticizer." The plasticizer influences the pliability and moldability of the implant composition such that it is rendered more comfortable to the patient when implanted. Moreover, the plasticizer has an effect upon the rate of sustained release of bioactive agent such that the rate can be increased or decreased according to the character of the plasticizer incorporated into the implant composition. In general, the biocompatible end-capped oligomeric liquid acting as a plasticizer is believed to facilitate molecular movement within the solid or gel thermoplastic matrix. The plasticizing capability enables polymer molecules of the matrix to move relative to each other so that pliability and easy moldability are provided. The plasticizing capability also enables easy movement of bioactive agent so that in some situations, the rate of sustained release is either positively or negatively affected.

A moderate to highly water soluble biocompatible end-capped oligomeric liquid can be generally used in the flowable compositions, especially when pliability should not be an issue after formation of the implant. Use of the highly water soluble biocompatible end-capped oligomeric liquid should provide an implant having the physical characteristics of an implant made through direct insertion of the flowable composition. A biocompatible end-capped oligomeric liquid of low or no water solubility may also be used in the sustained release delivery system. Preferably, a biocompatible end-capped oligomeric liquid of low or no water solubility is used when it is desirable to have an implant that remains pliable, is to be extrudable is to have an extended release and the like. For example, the release rate of the biologically active agent can be affected under some circumstances through the use of a biocompatible end-capped oligomeric liquid of low or no water solubility. Typically such circumstances involve retention of the biocompatible end-capped oligomeric liquid within the implant product and its function as a plasticizer or rate modifier.

Additionally, mixtures of the foregoing high and low or no solubility biocompatible end-capped oligomeric liquids providing varying degrees of solubility for the matrix forming material can be used to alter the life time, rate of bioactive agent release, and other characteristics of the implant.

Biodegradable Thermoplastic Polymer

In one embodiment, a flowable composition is produced by combining a solid, biodegradable thermoplastic polymer, bioactive agent, and a biocompatible end-capped oligomeric liquid. The flowable composition can be administered by a syringe and needle to a patient in need of treatment. Any suitable biodegradable thermoplastic polymer can be employed, provided that the biodegradable thermoplastic polymer is at least substantially insoluble in body fluid.

The biocompatible, biodegradable, thermoplastic polymer can be made from a variety of monomers, which form polymer chains or monomeric units joined together by linking groups. The thermoplastic polymer is composed of a polymer chain or backbone containing monomeric units joined by such linking groups as ester, amide, urethane, anhydride, carbonate, urea, esteramide, acetal, ketal, or orthocarbonate groups as well as any other organic functional group that can be hydrolyzed by enzymatic or hydrolytic reaction (i.e., is biodegradable by this hydrolytic action). The thermoplastic polymer is typically formed by reaction of starting monomers containing the reactant groups that should form the backbone linking groups. For example, alcohols and carboxylic acids should form ester linking groups. Isocyanates and amines or alcohols should respectively form urea or urethane linking groups.

Any aliphatic, aromatic, or arylalkyl starting monomer having the specified functional groups can be used to make the thermoplastic polymers, provided that the polymers and their degradation products are biocompatible. The monomer or monomers used in forming the thermoplastic polymer may be of a single or multiple identity. The resultant thermoplastic polymer should be a homopolymer formed from one monomer, or one set of monomers, for example, when a diol and diacid are used, or a copolymer, terpolymer, or multi-polymer formed from two or more, or three or more, or more than three monomers or sets of monomers. The biocompatibility specifications of such starting monomers are known in the art.

Useful thermoplastic polymers are substantially insoluble in aqueous media and body fluids, preferably completely insoluble in such media and fluids. They are also capable of dissolving or dispersing in selected biocompatible end-capped oligomeric liquids having a water solubility ranging from completely soluble in all proportions to water insoluble. The thermoplastic polymers also are biocompatible.

When used in the flowable composition, the thermoplastic polymer in combination with the biocompatible end-capped oligomeric liquid provides a viscosity of the flowable composition that varies from low viscosity, similar to that of water, to a high viscosity, similar to that of a paste, depending on the molecular weight and concentration of the thermoplastic polymer. Typically, the polymeric composition includes about 10 wt. % to about 95 wt. %, more preferably about 20 wt. % to about 70 wt. %, most preferably about 30 wt. % to about 60 wt. %, of a thermoplastic polymer.

In some embodiments, the biodegradable, biocompatible thermoplastic polymer can be a linear polymer, it can be a branched polymer, or it can be a combination thereof. Any option is available. To provide a branched thermoplastic polymer, some fraction of one of the starting monomers may be at least trifunctional, and preferably multifunctional. This multifunctional character provides at least some branching of the resulting polymer chain. For example, when the polymer chosen contains ester linking groups along its polymer backbone, the starting monomers normally should be hydroxycarboxylic acids, cyclic dimers of hydroxycarboxylic acids, cyclic trimers of hydroxycarboxylic acids, diols, or dicarboxylic acids. Thus, to provide a branched thermoplastic polymer, some fraction of a starting monomer that is at least multifunctional, for example, a triol or a tricarboxylic acid is included within the combination of monomers being polymerized to form the thermoplastic polymer. In addition, the polymers may incorporate more than one multifunctional unit per polymer molecule, and typically many multifunctional units depending on the stoichiometry of the polymerization reaction. The polymers may also optionally incorporate at least one multifunctional unit per polymer molecule. A so-called star or branched polymer is formed when one multifunctional unit is incorporated in a polymer molecule.

The preferred thermoplastic polyester may be formed from such monomers as hydroxycarboxylic acids or dimers thereof. Alternatively, a thermoplastic polyester may be formed from a dicarboxylic acid and a diol. A branching monomer, for example, a dihydroxycarboxylic acid would be included with the first kind of starting monomer, or a triol and/or a tricarboxylic acid would be included with the second kind of starting monomer if a branched polyester were desired. Similarly, a triol, tetra-ol, penta-ol, or hexa-ol, for example, sorbitol or glucose can be included with the first kind of starting monomer if a branched or star polyester were desired. The same rationale would apply to polyamides. A triamine and/or triacid would be included with starting monomers of a diamine and dicarboxylic acid. An amino dicarboxylic acid, diamino carboxylic acid, or a triamine would be included with the second kind of starting monomer, amino acid. Any aliphatic, aromatic, or arylalkyl starting monomer having the specified functional groups can be used to make the branched thermoplastic polymers, provided that the polymers and their degradation products are biocompatible. The biocompatibility specifications of such starting monomers are known in the art.

The monomers used to make the biocompatible thermoplastic polymers should produce polymers or copolymers that are thermoplastic, biocompatible, and biodegradable. Examples of thermoplastic, biocompatible, biodegradable polymers suitable for use as the biocompatible thermoplastic branched polymers include polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), and copolymers, terpolymers, combinations, or mixtures of the above materials. Suitable examples of such biocompatible, biodegradable, thermoplastic polymers are disclosed, e.g., in U.S. Pat. Nos. 4,938,763, 5,278,201, 5,312, 519, 5,702,716, 5,744,153, 5,990,194, 6,461,631, and 6,565, 874.

The polymer compositions can also include polymer blends of the polymers with other biocompatible polymers, so long as they do not interfere undesirably with the biodegradable characteristics of the composition. Blends of the polymers with such other polymers may offer even greater flexibility in designing the precise release profile desired for targeted drug delivery or the precise rate of biodegradability desired for implants.

The preferred biocompatible thermoplastic polymers or copolymers are those which have a lower degree of crystallization and are more hydrophobic. These polymers and copolymers are more soluble in the biocompatible end-capped oligomeric liquids than highly crystalline polymers, for example, polyglycolide, which has a high degree of hydrogen-bonding. Preferred materials with the desired solubility parameters are polylactides, polycaprolactones, and copolymers of these with glycolide so as to provide more amorphous regions to enhance solubility. Generally, the biocompatible, biodegradable thermoplastic polymer is substantially soluble in the biocompatible end-capped oligomeric liquid so that solutions, dispersions, or mixtures up to 50-60 wt. % solids can be made. Preferably, the polymers are typically completely soluble in the biocompatible end-capped oligomeric liquid so that solutions, dispersions, or mixtures up to 85-98 wt. % solids can be made. The polymers also are at least substantially insoluble in water so that less than 0.1 g of polymer per mL of water should dissolve or disperse in water. Preferably, the polymers are typically completely insoluble in water so that less than 0.001 g of polymer per mL of water should dissolve or disperse in water. At this preferred level, the flowable composition with a completely water miscible biocompatible end-capped oligomeric liquid should almost immediately transform to the solid implant.

The polymer compositions can also include a biocompatible, biodegradable PLG low-burst copolymer material adapted for use in a controlled release formulation, the low-burst copolymer material being characterized by a weight average molecular weight of about 10 kilodaltons to about 50 kilodaltons and a polydispersity index of about 1.4 to about 2.0, and being further characterized by having separated therefrom a copolymer fraction characterized by a weight average molecular weight of about 4 kDa to about 10 kDa and a polydispersity index of about 1.4 to about 2.5 (hereinafter the "removed copolymer fraction"). The PLG low-burst copolymer material is prepared from a starting PLG copolymer material without a step of hydrolysis of a higher molecular weight PLG copolymer material, by dissolving the starting copolymer material, which is not a product of hydrolysis of a higher molecular weight PLG copolymer material, in a solvent, then precipitating the low-burst copolymer material with a non-solvent. This process, as applied to a starting material that has never been subjected to hydrolysis, separates out an amount of the removed copolymer fraction effective to confer desirable controlled release properties including low initial burst upon the copolymer. These materials, also known as PLGHp, are disclosed in copending and commonly-assigned U.S. Patent Application Ser. No. 60/901,435, filed Feb. 15, 2007, entitled "LOW-BURST POLYMERS AND METHODS TO PRODUCE POLYMERS," which is hereby incorporated by reference.

Optionally, the delivery system may also contain a combination of a non-polymeric material and an amount of a thermoplastic polymer. The combination of non-polymeric material and thermoplastic polymer may be adjusted and designed to provide a more coherent bioactive agent sustained release delivery system.

Non-polymeric materials that may be useful include those that are biocompatible, substantially insoluble in water and body fluids, and biodegradable and/or bioerodible within the body of an animal. The non-polymeric material is capable of being at least partially solubilized in a biocompatible end-capped oligomeric liquid. In the flowable compositions containing some biocompatible end-capped oligomeric liquid or other additive, the non-polymeric materials are also capable of coagulating or solidifying to form a solid or gel implant upon the dissipation, dispersement or leaching of the biocompatible end-capped oligomeric liquid component from the flowable composition upon contact of the flowable composition with a body fluid. The matrix of all embodiments of the implant including a non-polymeric material should have a consistency ranging from gelatinous to impressionable and moldable, to a hard, dense solid.

Non-polymeric materials that can be used in the delivery system generally include any having the foregoing characteristics. Useful non-polymeric materials include sterols, for example, cholesterol, stigmasterol, beta-sistosterol, and estradiol; cholestery esters such as cholesteryl stearate, $C_{18}$-$C_{36}$ mono-, di-, and tricylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl tridocosanoate, glyceryl trimyristate, glyceryl tridecenoate, glyceryl tristearate, and mixtures thereof; sucrose fatty acid esters such as sucrose distearate and sucrose palmitate; sorbitan fatty acid esters such as sorbitan monostearate, sorbitan monopalmitate, and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glyceryl tristearate, stearic acid, stearic anhydride, glyceryl monooleate, glyceryl monolinoleate, and acetylated monoglycerides.

The polymeric and non-polymeric materials may be selected and/or combined to control the rate of biodegradation, bioerosion and/or bioabsorption within the implant site. Generally, the implant matrix should breakdown over a period from about 1 week to about 12 months, preferably over a period of about 1 week to about 4 months.

Thermoplastic Polymer Molecular Weight

The molecular weight of the polymers can affect the rate of bioactive agent release from the implant. Typically, under these conditions, as the molecular weight of the polymer increases, the rate of bioactive agent release from the system decreases. This phenomenon can be advantageously used in the formulation of systems for the controlled release of bioactive agent. For relatively quick release of bioactive agent, low molecular weight polymers can be chosen to provide the desired release rate. For release of bioactive agent over a relatively long period of time, a higher polymer molecular weight can be chosen. Accordingly, a bioactive agent, a metabolite, or a prodrug thereof, sustained release delivery system can be produced with an optimum polymer molecular weight range for the release of bioactive agent over a selected length of time.

The molecular weight of a polymer can be varied by any of a variety of methods. The choice of method is typically determined by the polymer formation method. Typically, the ratio of initiator to monomer (i.e., cyclic dimer) may be used for an addition polymerization. The ratio of monofunctional reactant to monomers may be used for condensation polymerization. Alternately, if a thermoplastic polyester is used that is degradable by hydrolysis, the molecular weight can be varied by controlled hydrolysis, such as in a steam autoclave. In general, the degree of polymerization can be controlled, for example, by varying the number and type of reactive groups and the reaction times.

The control of molecular weight and/or inherent viscosity of the thermoplastic polymer are factors involved in the formation and performance of the implant. In general, thermoplastic polymers with higher molecular weight and higher inherent viscosity should provide an implant with a slower degradation rate and therefore a longer duration.

Suitable thermoplastic polymers may have average molecular weights ranging from about 1 kiloDalton (kDa) to about 100 kDa, preferably from about 10,000 to about 45,000, or more preferably from about 15,000 to about 40,000.

The molecular weight may also be indicated by the inherent viscosity (abbreviated as "I.V.", units are in deciliters/ gram). Generally, the inherent viscosity of the thermoplastic polymer is a measure of its molecular weight and degradation time (e.g., a thermoplastic polymer with a high inherent viscosity has a higher molecular weight and longer degradation time). Preferably, the thermoplastic polymer has a molecular weight, as shown by the inherent viscosity, from about 0.05 dL/g to about 2.0 dL/g (as measured in chloroform), more preferably from about 0.10 dL/g to about 0.8 dL/g.

Characteristics of Preferred Polyester

The preferred thermoplastic biodegradable polymer of the flowable compositions is a polyester. Generally, the polyester may be composed of units of one or more $C_2$ to $C_{10}$ hydroxycarboxylic acid residues wherein the distribution of differing units may be random, block, paired, or sequential. Alternatively, the polyester may be composed of units of one or more $C_2$ to $C_{12}$ diols and one or more $C_3$ to $C_{12}$ dicarboxylic acids. The distribution should depend upon the starting materials used to synthesize the polyester and upon the process for synthesis. An example of a polyester composed of differing paired units distributed in block or sequential fashion is a poly(lactide-co-glycolide). An example of a polyester composed of differing unpaired units distributed in random fashion is poly(lactic acid-co-glycolic acid). Other examples of suitable biodegradable thermoplastic polyesters include polylactides, polyglycolides, polycaprolactones, copolymers thereof, terpolymers thereof, and any combinations thereof. Preferably, the suitable biodegradable thermoplastic polyester is a polylactide, a polyglycolide, a copolymer thereof, a terpolymer thereof, or a combination thereof.

The terminal groups of the poly(DL-lactide-co-glycolide) can either be hydroxyl, carboxyl, or ester depending upon the method of polymerization. Polycondensation of lactic or glycolic acid should provide a polymer with terminal hydroxyl and carboxyl groups. Ring-opening polymerization of the cyclic lactide or glycolide monomers with water, lactic acid, or glycolic acid should provide polymers with these same terminal groups. However, ring-opening of the cyclic monomers with a monofunctional alcohol, for example, methanol, ethanol, or 1-dodecanol should provide a polymer with one hydroxyl group and one ester terminal group. Ring-opening polymerization of the cyclic monomers with a polyol, for example, glucose, 1,6-hexanediol, or polyethylene glycol should provide a polymer with hydroxyl terminal groups. Such a polymerization of dimers of hydroxycarboxylic acids and a polyol is a chain extension of the polymer. The polyol acts as a central condensation point with the polymer chain growing from the hydroxyl groups incorporated as ester moieties of the polymer. The polyol may be a diol, triol, tetraol, pentaol, or hexaol of 2 to 30 carbons in length. Examples include saccharides, reduced saccharides such as sorbitol, diols such as hexane-1,6-diol, triols such as glycerol or reduced fatty acids, and similar polyols. Generally, the polyesters copolymerized with alcohols or polyols should provide longer duration implants.

The type, molecular weight, and amount of the preferred biodegradable thermoplastic polyester present in the flowable composition should typically depend upon the desired properties of the controlled sustained release implant. For example, the type, molecular weight, and amount of biodegradable thermoplastic polyester can influence the length of time in which the bioactive agent, a metabolite, or a prodrug thereof, is released from the controlled sustained release implant. Specifically, in one embodiment, the composition can be used to formulate a one month sustained release delivery system of bioactive agent. In such an embodiment, the biodegradable thermoplastic polyester can be a 50/50, 55/45, 75/25, 85/15, 90/10, or 95/5 poly(DL-lactide-co-glycolide) having a carboxy terminal group, preferably a 50/50 poly(DL-lactide-co-glycolide) having a carboxy terminal group; can be present in about 20 wt. % to about 70 wt. % of the composition; and can have an average molecular weight of about 10,000 to about 45,000 or about 15,000 to about 40,000.

In another embodiment, the flowable composition can be formulated to provide a three month sustained release delivery system of bioactive agent. In such an embodiment, the biodegradable thermoplastic polyester can be a 50/50, 55/45, 75/25, 85/15, 90/10, or 95/5 poly(DL-lactide-co-glycolide) without a carboxy terminal group; preferably be a 75/25 poly(DL-lactide-co-glycolide) without a carboxy terminal group; can be present in about 20 wt. % to about 70 wt. % of the composition; and can have an average molecular weight of about 10,000 to about 45,000 or about 15,000 to about 40,000; or can be an 85/15 poly(DL-lactide-co-glycolide) containing a 1,6-hexane diol chain extender, at a weight percentage of about 20 wt. % to about 70 wt. % of the flowable composition and at an average molecular weight of about 10,000 to about 45,000 or about 15,000 to about 40,000. Any polyester that has a terminal carboxyl group can optionally be extended with a $C_2$ to $C_{12}$ diol moiety.

Organic Liquids

Some embodiments may also contain organic liquids in addition to the biocompatible end-capped oligomeric liquids. Suitable organic liquids used in addition to the biocompatible end-capped oligomeric liquids include, for example, aliphatic, aryl, and arylalkyl; linear, cyclic, and branched organic compounds that are liquid or at least flowable at ambient and physiological temperature and contain such functional groups as alcohols, alkoxylated alcohols, ketones, ethers, polymeric ethers, amides, esters, carbonates, sulfoxides, sulfones, any other functional group that is compatible with living tissue, and any combination thereof. The organic liquid used in addition to the biocompatible end-capped oligomeric liquids preferably is a polar aprotic, or polar protic organic solvent. Preferably, the organic liquid has a molecular weight in the range of about 30 to about 1000.

Preferred organic liquids that are used in addition to the biocompatible end-capped oligomeric liquids include, for example, N-methyl-2-pyrrolidone, 2-pyrrolidone; $C_1$ to $C_{15}$ alcohols, diols, triols, and tetraols such as ethanol, glycerin, propylene glycol, and butanol; $C_3$ to $C_{15}$ alkyl ketones such as acetone, diethyl ketone, and methyl ethyl ketone; $C_3$ to $C_{15}$ esters and alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; $C_1$ to $C_{15}$ amides such as dimethylformamide, dimethylacetamide, and caprolactam; $C_3$ to $C_{20}$ ethers such as tetrahydrofuran or solketal; tweens, triacetin, decylmethylsulfoxide, dimethyl sulfoxide, oleic acid, 1-dodecylazacycloheptan-2-one, N-methyl-2-pyrrolidone, esters of carbonic acid and alkyl alcohols such as propylene carbonate, ethylene carbonate, and dimethyl carbonate; alkyl ketones such as acetone and methyl ethyl ketone; alcohols such as solketal, glycerol formal, and glycofurol; dialkylamides such as dimethylformamide, dimethylacetamide, dimethylsulfoxide, and dimethylsulfone; lactones such as epsilon-caprolactone and butyrolactone; cyclic alkyl amides such as caprolactam; triacetin and diacetin; aromatic amides such as N,N-dimethyl-m-toluamide, and mixtures and combinations thereof. Preferred organic liquids that are used in addition to the biocompatible end-capped oligomeric liquids include, for example, N-methyl-2-pyrrolidone, 2-pyrrolidone, dimethylsulfoxide, ethyl lactate, propylene carbonate, solketal, triacetin, glycerol formal, isopropylidene glycol, and glycofurol.

Other preferred organic liquids that are used in addition to the biocompatible end-capped oligomeric liquids include, for example, benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred organic liquids that are used in addition to the biocompatible end-capped oligomeric liquids are N-methyl-2-pyrrolidone, 2-pyrrolidone, dimethyl sulfoxide, triacetin, and propylene carbonate because of their solvating ability and their compatibility.

Bioactive Agent

The flowable compositions may contain one or more bioactive agents. The bioactive agent/s may be any pharmaceutical small molecule or biological compound that causes a pharmacological, biological and/or physiological effect when administered to a mammal such as a human. The effect may be intrinsic in that it ameliorates, prevents, minimizes or otherwise treats an organic malcondition of the mammal, or the effect may be extrinsic in that it ameliorates, prevents, minimizes or otherwise treats a malcondition of the mammal caused by an exogenous agent.

Suitable bioactive agents may include, for example, anabolic agents, antacids, anti-asthmatic agents, anti-cholesterolemic and anti-lipid agents, anti-coagulants, anti-convulsants, anti-diarrheals, anti-emetics, anti-infective agents, antibacterial agents, antimicrobial agents, anti-inflammatory agents, anti-manic agents, antimetabolite agents, anti-nauseants, anti-neoplastic agents, anti-obesity agents, anti-pyretic agents, analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, antigenic materials, or a combination thereof.

Suitable bioactive agents may include, for example, androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestyramine, N-acetylprocainamide, acetaminophen, aspirin, ibuprofen, phenylpropanolamine hydrochloride, caffeine, guaifenesin, aluminum hydroxide, magnesium hydroxide, peptides, polypeptides, proteins, amino acids, interferons, cytokines, vaccines, or a combination thereof.

Suitable bioactive agents may include, for example, peptide drugs, protein drugs, desensitizing materials, antigens, anti-infective agents, antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, the benzophenanthridine alkaloids, or a combination thereof. The bioactive agent, a metabolite, or a prodrug thereof, may further be a substance capable of acting as, for example, a stimulant, sedative, hypnotic, analgesic, anticonvulsant, and the like.

Suitable bioactive agents may include, for example, 16-alpha fluoroestradiol, 16-alpha-gitoxin, 16-epiestriol, 17-alpha dihydroequilenin, 17-alpha estradiol, 17-beta estradiol, 17-hydroxy progesterone, 1-alpha-hydroxyvitamin D2, 1-dodecpyrrolidinone, 20-epi-1,25 dihydroxyvitamin D3, 22-oxacalcitriol, 2CW, 2'-nor-cGMP, 3-isobutyl GABA, 5-ethynyluracil, 6-FUDCA, 7-methoxytacrine, Abamectin, abanoquil, abecarnil, abiraterone, Ablukast, Ablukast Sodium, Acadesine, acamprosate, Acarbose, Acebutolol, Acecamide Hydrochloride, Aceclidine, aceclofenae, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, adafenoxate, adapalene, Adapalene, adatanserin, Adatanserin Hydrochloride, adecypenol, adecypenol, Adefovir, adelmidrol, ademetionine, Adenosine, Adinazolam, Adipheinine Hydrochloride, adiposin, Adozelesin, adrafinil, Adrenalone, airbutamine, alacepril, Alamecin, Alanine, Alaproclate, alaptide, Albendazole, albolabrin, Albuterol, Albutoin, Alclofenae, Alclometasone Dipropionate, Alcloxa, aldecalmycin, Aldesleukin, Aldioxa, Alendronate Sodium, alendronic acid, alentemol, Alentemol Hydrobromide, Aletamine Hydrochloride, Aleuronium Chloride, Alexidine, alfacalcidol, Alfentanil Hydrochloride, alfuzosin, Algestone Acetonide, alglucerase, Aliflurane, alinastine, Alipamide, Allantoin, Allobarbital, Allopurinol, ALL-TK antagonists, Alonimid, alosetron, Alosetron Hydrochloride, Alovudine, Alpertine, Alpha Amylase, alpha idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverine Citrate, Alvircept Sudotox, Amadinone Acetate, Amantadine Hydrochloride, ambamustine, Ambomycin, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amflutizole, Amicycline, Amidephrine Mesylate, amidox, Amifloxacin, amifostine, Amikacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, Amobarbital Sodium, Amodiaquine, Amodiaquine Hydrochloride, Amorolfine, Amoxapine, Amoxicillin, Amphecloral, Amphetamine Sulfate, Amphomycin, Amphotericin B, Ampicillin, ampiroxicam, Ampyzine Sulfate, Amquinate, Amrinone, aminone, amrubicin, Amsacrine, amylin, amythiamicin, Anagestone Acetate, anagrelide, Anakinra, ananain, anaritide, Anaritide Acetate, Anastrozole, Anazolene Sodium, Ancrod, andrographolide, Androstenedione, angiogenesis inhibitors, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramycin, antiandrogen, Acedapsone, Felbamate, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, aripiprazol, arotinolol, Arpinocid, Arteflene, Artilide Fumarate, asimadoline, aspalatone, Asparaginase, Aspartic Acid, Aspartocin, asperfuran, Aspirin, aspoxicillin, Asprelin, Astemizole, Astromicin Sulfate, asulacrine, atamestane, Atenolol, atevirdine, Atipamezole, Atiprosin Maleate, Atolide, Atorvastatin Calcium, Atosiban, Atovaquone, atpenin B, Atracurium Besylate, atrimustine, atrinositol, Atropine, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basifungin, Batanopride Hydrochloride, batebulast, Batelapine Maleate, Batimastat, beauvericin, Becanthone Hydrochloride, becaplermin, becliconazole, Beclomethasone Dipropionate, befloxatone, Beinserazide, Belfosdil, Belladonna, Beloxamide, Bemesetron, Bemitradine, Bemoradan, Benapryzine Hydrochloride, Benazepril Hydrochloride, Benazeprilat, Bendacalol Mesylate, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, Benzoylpas Calcium, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, beta-alethine, betaclamycin B, Betamethasone, betamipron, betaxolol, Betaxolol Hydrochloride, Bethanechol Chloride, Bethanidine Sulfate, betulinic acid, bevantolol, Bevantolol Hydrochloride, Bezafibrate, bFGF inhibitor, Bialamicol Hydrochloride, Biapenem, Bicalutamide, Bicifadine Hydrochloride, Biclodil Hydrochloride, Bidisomide, bifemelane, Bifonazole, bimakalim, bimithil, Bindarit, Biniramycin, binospirone, bioxalomycin alpha2, Bipenamol Hydrochloride, Biperiden, Biphenamine Hydrochloride, biriperone, bisantrene, bisaramil, bisaziridinylspermine, bis-benzimidazole A, bis-benzimidazole B, bisnafide, Bisobrin Lactate, Bisoprolol, Bispyrithione Magsulfex, bistramide D, bistramide K, bistratene A, Bithionolate Sodium, Bitolterol Mesylate, Bivalirudin, Bizelesin, Bleomycin Sulfate, Bolandiol Dipropionate, Bolasterone, Boldenone Undecylenate, boldine, Bolenol, Bolmantalate, bopindolol, Bosentan, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelains, bromfenac, Brominidione, Bromocriptine, Bromodiphenhydramine Hydrochloride, Bromoxamide, Bromperidol, Bromperidol Decanoate, Brompheniramine Maleate, Broperamole, Bropirimine, Brotizolam, Bucamide Maleate, bucindolol, Buclizine Hydrochloride, Bucromarone, Budesonide, budipine, budotitane, Buformin, Bumetamide, Bunaprolast, bunazosin, Bunolol Hydrochloride, Bupicomide, Bupivacaine Hydrochloride, Buprenorphine Hydrochloride, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthionine sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, camonagrel, camptothecin derivatives, canarypox IL-2, candesartan, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbocysteine, Carbol-Fuchsin, Carboplatin, Carboprost, carbovir, carboxamide-amino-triazole, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Camidazole, Caroxazone, carperitide, Carphenazine Maleate, Carprofen, Carsatrin Succinate, Cartazolate, carteolol, Carteolol Hydrochloride, cartilage derived inhibitor, Carubicin Hydrochloride, Carumonam Sodium, carvedilol, carvotroline, Carvotroline Hydrochloride, carzelesin, casein kinase inhibitors (ICOS), castanospermine, caurumonam, cebaracetam, cecropin B, Cedefingol, Cefaclor, Cefadroxil, Cefamandole, Cefaparole, Cefatrizine, Cefazaflur Sodium, Cefazolin, Cefbuperazone, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefinetazole, cefminlox, cefodizime, Cefonicid Sodium, Cefoperazone Sodium, Ceforamide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxone, Cefuroxime, celastrol, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceronapril, certoparin sodium, Ceruletide, Cetaben Sodium, Cetalkonium Chloride, Cetamolol Hydrochloride, cetiedil, cetirizine, Cetophenicol, Cetraxate Hydrochloride, cetrorelix, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphenesin Carbamate, chlorpheniramine Maleate, Chlorpromazine, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin Sodium, Cilazapril, cilnidipine, Cilobamine Mesylate, cilobradine, Cilofungin, cilostazol, Cimaterol, Cimetidine, cimetropium bromide, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, cisapride, cisatracurium besilate, Cisconazole, Cisplatin, cisporphyrin, cistinexine, citalopram, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, Clioquinol, Clioxamide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Clogestone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonitrate, Clonixeril, Clonixin, Clopamide, Clopenthixol, Cloperidone Hydrochloride, clopidogrel, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortermine Hydrochloride, Closantel, Closiramine Aceturate, Clothiapine, Clothixamide Maleate Cloticasone Propionate, Clotrimazole, Cloxacillin Benzathine, Cloxyquin, Clozapine, Cocaine, Coccidioidin, Codeine, Codoxime, Colchicine, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, combretastatin analogue, complestatin, conagenin, Conorphone Hydrochloride, contignasterol, contortrostatin, Cormethasone Acetate, Corticorelin Ovine Triflutate, Corticotropin, Cortisone Acetate, Cortivazol, Cortodoxone, cosalane, costatolide, Cosyntropin, cotinine, Coumadin, Coumermycin, crambescidin 816, Crilvastatin, crisnatol, Cromitrile Sodium, Cromolyn Sodium, Crotamiton, cryptophycin 8, cucumariosid, Cuprimyxin, curacin A, curdlan sulfate, curiosin, Cyclacillin, Cyclazocine, cyclazosin, cyclic HPMPC, Cyclindole, Cycliramine Maleate, Cyclizine, Cyclobendazole, cyclobenzaprine, cyclobut A, cyclobut G, cyclocapron, Cycloguanil Pamoate, Cyclohex- imide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cypenamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine Ocfosfate, cytochalasin B, cytolytic factor, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, daphlnodorin A, dapiprazole, dapitant, Dapoxetine Hydrochloride, Dapsone, Daptomycin, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, deslorelin, desmopressin, desogestrel, Desonide, Desoximetasone, desoxoamiodarone, Desoxycorticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, Dexivacaine, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichliorvos, Dichloralphenazone, Dichlorphenamide, Dicirenone, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, dihydrotaxol, 9-, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, dimethyl prostaglandin A1, Dimethyl Sulfoxide, dimethylhomospermine, dimiracetam, Dimoxamine Hydrochloride, Dinoprost, Dinoprostone, Dioxadrol Hydrochloride, dioxamycin, Diphenhydramine Citrate, Diphenidol, Diphenoxylate Hydrochloride, diphenyl spiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfuram, Ditekiren, Divalproex Sodium, Dizocilpine Maleate, Dobutamine, docarpamine, Docebenone, Docetaxel, Doconazole, docosanol, dofetilide, dolasetron, Ebastine, ebiratide, ebrotidine, ebselen, ecabapide, ecabet, ecadotril, ecdisteron, echicetin, echistatin, Echothiophate Iodide, Eclanamine Maleate, Eclazolast, ecomustine, Econazole, ecteinascidin 722, edaravone, Edatrexate, edelfosine, Edifolone Acetate, edobacomab, Edoxudine, edrecolomab, Edrophonium Chloride, edroxyprogesteone Acetate, efegatran, eflornithine, efonidipine, egualcen, Elantrine, eleatonin, elemene, eletriptan, elgodipine, eliprodil, Elsamitrucin, eltenae, Elucaine, emalkalim, emedastine, Emetine Hydrochloride, emiglitate, Emilium Tosylate, emitefur, emoctakin, Enadoline Hydrochloride, enalapril, Enalaprilat, Enalkiren, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, epristeride, Eprosartan, eptastigmine, equilenin, Equilin, Erbulozole, erdosteine, Ergoloid Mesylates, Ergonovine Maleate, Ergotamine Tartrate, ersentilide, Ersofermin, erythritol, Erythrityl Tetranitrate, Erythromycin, Esmolol Hydrochloride, Esorubicin Hydrochloride, Esproquin Hydrochloride, Estazolam, Estradiol, Estramustine, estramustine analogue, Estrazinol Hydrobromide, Estriol, Estrofurate, estrogen agonists, estrogen antagonists, Estrogens, Conjugated, Estrogens, Esterified, Estrone, Estropipate, esuprone, Etafedrine Hydrochloride, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ether, Ethinyl estradiol, Ethiodized Oil, Ethionamide, Ethonam Nitrate, Ethopropazine Hydrochloride, Ethosuximide, Ethotoin, Ethoxazene Hydrochloride, Ethybenztropine, Ethyl Chloride, Ethyl Dibunate, Ethylestrenol, Ethyndiol, Ethynerone, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, Etoxadrol Hydrochloride, Etozolin, etrabamine, Etretinate, Etryptamine Acetate, Eucatropine Hydrochloride, Eugenol, Euprocin Hydrochloride, eveminomicin, Exametazime, examorelin, Exaprolol Hydrochloride, exemestane, fadrozole, faeriefungin, Famciclovir, Famotidine, Fampridine, fantofarone, Fantridone Hydrochloride, faropenem, fasidotril, fasudil, fazarabine, fedotozine, felbamate, Felbinac, Felodipine, Felypressin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, fenofibrate, fenoldopam, Fenoprofen, Fenoterol, Fenpipalone, Fenprinast Hydrochloride, Fenprostalene, Fenquizone, fenretinide, fenspiride, Fentanyl Citrate, Fentiazac, Fenticlor, fenticonazole, Fenyripol Hydrochloride, fepradinol, ferpifosate sodium, ferristene, ferrixan, Ferrous Sulfate, Dried, Ferumoxides, ferumoxsil, Fetoxylate Hydrochloride, fexofenadine, Fezolamine Fumarate, Fiacitabine, Fialuridine, Fibrinogen I 125, filgrastim, Filipin, finasteride, Flavodilol Maleate, flavopiridol, Flavoxate Hydrochloride, Flazalone, flecamide, flerobuterol, Fleroxacin, flesinoxan, Flestolol Sulfate, Fletazepam, flezelastine, flobufen, Floctafenine, flomoxef, Flordipine, florfenicol, florifenine, flosatidil, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose F 18, Fludorex, Fludrocortisone Acetate, Flufenamic Acid, Flufenisal, Flumazenil, flumecinol, Flumequine, Flumeridone, Flumethasone, Flumetramide, Flumezapine, Fluminorex, Flumizole, Flumoxonide, flunarizine, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa F 18, Fluorometholone, Fluorouracil, Fluotracen Hydrochloride, Fluoxetine, Fluoxymesterone, fluparoxan, Fluperamide, Fluperolone Acetate, Fluphenazine Decanoate, flupirtine, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, flurithromycin, Fluorocitabine, Fluorofamide, Fluorogestone Acetate, Fluorothyl, Fluoroxene, Fluspiperone, Fluspirilene, Fluticasone Propionate, flutrimazole, Flutroline, fluvastatin, Fluvastatin Sodium, fluvoxamine, Fluzinamide, Folic Acid, Follicle regulatory protein, Folliculostatin, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinoprilat, fosphenyloin, Fosquidone, Fostedil, fostriecin, fotemustine, Fuchsin, Basic, Fumoxicillin, Fungimycin, Furaprofen, Furazolidone, Furazolium Chloride, Furegrelate Sodium, Furobufen, Furodazole, Furosemide, Fusidate Sodium, Fusidic Acid, gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, gelatinase inhibitors, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glaspimod, glaucocalyxin A, Glemanserin, Gliamilide, Glibornuride, Glicetanile Sodium, Gliflumide, Glimepiride, Glipizide, Gloximonam, Glucagon, glutapyrone, glutathione inhibitors, Glutethimide, Glyburide, glycopine, glycopril, Glycopyrrolate, Glyhexamide, Glymidine Sodium, Glyoctamide, Glyparamide, Gold Au 198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, Han memopausal gonadotropins, hatomamicin, hatomarubigin A, hatomarubigin B, hatomarubigin C, hatomarubigin D, Heparin Sodium, hepsulfam, heregulin, Hetacillin, Heteronium Bromide, Hexachlorophene:Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, Homatropine Hydrobromide, Hoquizil Hydrochloride, Human chorionic gonadotropin, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurca, Hydroxyzine Hydrochloride, Hymecromone, Hyoscyamine, hypericin, Ibafloxacin, ibandronic acid, ibogaine, Ibopamine, ibudilast, Ibufenac, Ibuprofen, Ibutilide Fumarate, Icatibant Acetate, Ichthammol, Icotidine, idarubicin, idoxifene, Idoxuridine, idramantone, Iemefloxacin, Iesopitron, Ifetroban, Ifosfamide, Ilepeimide, illimaquinone, ilmofosine, ilomastat, Ilonidap, iloperidone, iloprost, Imafen Hydrochloride, Imazodan Hydrochloride, imidapril, imidazenil, imidazoacridones, Imidecyl Iodine, Imidocarb Hydrochloride, Imidoline Hydrochloride, Imidurea, Imiloxan Hydrochloride, Imipenem, Imipramine Hydrochloride, imiquimod, immunostimulant peptides, Impromidine Hydrochloride, Indacrinone, Indapamide, Indecamide Hydrochloride, Indeloxazine Hydrochloride, Indigotindisulfonate Sodium, indinavir, Indocyanine Green, Indolapril Hydrochloride, Indolidan, indometacin, Indomethacin Sodium, Indoprofen, indoramin, Indorenate Hydrochloride, Indoxole, Indriline Hydrochloride, inocoterone, inogatran, inolimomab, Inositol Niacinate, Insulin, interferons, interleukins, Intrazole, Intriptyline Hydrochloride, iobenguane, Iobenzamic Acid, iobitridol, Iocarmate Meglumine, Iocarmic Acid, Iocetamic Acid, Iodamide, Iodine, Iodipamide Meglumine, Iodixanol, iodoamiloride, Iodoantipyrine I 131, Iodocholesterol I 131, iododoxorubicin, Iodohippurate Sodium I 131, Iodopyracet I 125, Iodoquinol, Iodoxamate Meglumine, Iodoxamie Acid, Ioglicic Acid, Iofetamine Hydrochloride I 123, iofratol, Ioglucol, Ioglucomide, Ioglycamic Acid, Iogulamide, Iohexyl, iomeprol, Iomethin I 125, Iopamidol, Iopanoic Acid, iopentol, Iophendylate, Ioprocemic Acid, iopromide, Iopronic Acid, Iopydol, Iopydone, iopyrol, Iosefamic Acid, Ioseric Acid, Iosulamide Meglumine, Iosumetic Acid, Iotasul, Iotetric Acid, Iothalamate Sodium, Iothalamic Acid, iotriside, Iotrolan, Iotroxic Acid, Iotyrosine I 131, Ioversol, Ioxagiate Sodium, Ioxaglate Meglumine, Ioxaglic Acid, ioxilan, Ioxotrizoic Acid, ipazilide, ipenoxazone, ipidacrine, Ipodate Calcium, ipomeanol, 4-, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladine, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isofluorophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, jasplakinolide, Josamycin, kahalalide F, Kalafungin, Kanamycin Sulfate, Ketamine Hydrochloride, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, laennec, lafutidine, lamellarin-N triacetate, lamifiban, Lamivudine, Lamotrigine, lanoconazole, Lanoxin, lanperisone, lanreotide, Lansoprazole, latanoprost, lateritin, laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, Leuprolide Acetate, leuprolide+estrogen+progesterone–, leuprorelin, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizine, Lifibrate, Lifibrol, Linarotene, Lincomycin, linear polyamine analogue, Linogliride, Linopirdine, linotroban, linsidomine, lintitript, lintopride, Liothyronine I 125, liothyronine sodium, Liotrix, lirexapride, lisinopril, lissoclinamide 7, Lixazinone Sulfate, lobaplatin, Lobenzarit Sodium, Lobucavir, Lodelaben, lodoxamide, Lofemizole Hydrochloride, Lofentanil Oxalate, Lofepramine Hydrochloride, Lofexidine Hydrochloride, lombricine, Lomefloxacin, lomerizine, Lometraline Hydrochloride, lometrexol, Lomofungin, Lomoxicam, Lomustine, Lonapalene, lonazolac, lonidamine, Loperamide Hydrochloride, loracarbef, Lorajmine Hydrochloride, loratadine, Lorazepam, Lorbamate, Lorcamide Hydrochloride, Loreclezole, Loreinadol, lorglumide, Lormetazepam, Lornoxicam, lornoxicam, Lortalamine, Lorzafone, losartan, losigamone, losoxantrone, Losulazine Hydrochloride, loteprednol, lovastatin, loviride, Loxapine, Loxoribine, lubeluzole, Lucanthone Hydrochloride, Lufironil, Lurosetron Mesylate, lurtotecan, luteinizing hormone, lutetium, Lutrelin Acetate, luzindole, Lyapolate Sodium, Lycetamine, lydicamycin, Lydimycin, Lynestrenol, Lypressin, Lysine, lysofylline, lysostaphin, lytic peptides, Maduramicin, Mafenide, magainin 2 amide, Magnesium Salicylate, Magnesium Sulfate, magnolol, maitansine, Malethamer, mallotochromene, mallotojaponin, Malotilate, malotilate, mangafodipir, manidipine, maniwamycin A, Mannitol, mannostatin A, manumycin E, manumycin F, mapinastine, Maprotiline, marimastat, Martek 158708, Martek 92211, Masoprocol, maspin, massetolide, matrilysin inhibitors, Maytansine, Mazapertine Succinate, Mazindol, Mebendazole, Mebeverine Hydrochloride, Mebrofenin, Mebutamate, Mecamylamine Hydrochloride, Mechlorethamine Hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Melitracen Hydrochloride, Melphalan, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Mercury, Ammoniated, Merisoprol Hg 197, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, Methadone Hydrochloride, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, Methoxyflurane, Methsuximide, Methyclothiazide, Methyl 10 Palmoxirate, Methylatropine Nitrate, Methylbenzethonium Chloride, Methyldopa, Methyldopate Hydrochloride, Methylene Blue, Methylergonovine Maleate, methylhistamine, R-alpha, methylinosine monophosphate, Methylphenidate Hydrochloride, Methylprednisolone, Methyltestosterone, Methynodiol Diacetate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoquizine, Metrifonate, Metrizamide, Metrizoate Sodium, Metronidazole, Meturedepa, Metyrapone, Metyrosine, Mexiletine Hydrochloride, Mexrenoate Potassium, Mezlocillin, mfonelic Acid, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minoxidil, Mioflazine Hydrochloride, miokamycin, mipragoside, mirfentanil, mirimostim, Mirincamycin Hydrochloride, Mirisetron Maleate, Mirtazapine, mismatched double stranded RNA, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecamide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, Montelukast Sodium, montirelin, mopidamol, moracizine, Morantel Tartrate, Moricizine, Morniflumate, Morphine Sulfate, Morrhuate Sodium, mosapramine, mosapride, motilide, Motretinide, Moxalactam Disodium, Moxazocine, moxiraprine, Moxnidazole, moxonidine, Mumps Skin Test Antigen, mustard anticancer agent, Muzolimine, mycaperoxide B, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Nalidixate Sodium, Nalidixic Acid, nalmefene, Nalmexone Hydrochloride, naloxone+pentazocine, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxol, napsagatran, Naranol Hydrochloride, Narasin, naratriptan, nartograstim, nasaruplase, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, neutral endopeptidase, Neutramycin, Nevirapine, Nexeridine Hydrochloride, Niacin, Nibroxane, Nicardipine Hydrochloride, Nicergoline, Niclosamide, Nicorandil, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, nilutamide, Nilvadipine, Nimazone, Nimodipine, niperotidine, niravoline, Niridazole, nisamycin, Nisbuterol Mesylate, nisin, Nisobamate, Nisoldipine, Nisoxetine, Nisterime Acetate, Nitarsone, nitazoxamide, nitecapone, Nitrafudam Hydrochloride, Nitralamine Hydrochloride, Nitramisole Hydrochloride, Nitrazepam, Nitrendipine, Nitrocycline, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfloxacin, Norflurane, Norgestimate, Norgestomet, Norgestrel, Nortriptyline Hydrochloride, Noscapine, Novobiocin Sodium, N-substituted benzaimides, Nufenoxole, Nylestriol, Nystatin, O6-benzylguanine, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Oformine, okicenone, Olanzapine, oligonucleotides, olopatadine, olprinone, olsalazine, Olsalazine Sodium, Olvanil, omeprazole, onapristone, ondansetron, Ontazolast, Oocyte maturation inhibitor, Opipramol Hydrochloride, oracin, Orconazole Nitrate, Orgotein, Orlislat, Ormaplatin, Ormetoprim, Ornidazole, Orpanoxin, Orphenadrine Citrate, osaterone, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenpropionate, Oxolinic Acid, Oxprenolol Hydrochloride, Oxtriphylline, Oxybutynin Chloride, Oxychlorosene, Oxycodone, Oxymetazoline Hydrochloride, Oxymetholone, Oxymorphone Hydrochloride, Oxypertine, Oxyphenbutazone, Oxypurinol, Oxytetracycline, Oxytocin, ozagrel, Ozolinone, Paclitaxel, palauamine, Paldimycin, palinavir, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, parthenolide, Partricin, Paulomycin, pazelliptine, Pazinaclone, Pazoxide, pazufloxacin, pefloxacin, pegaspargase, Pegorgotein, Pelanserin Hydrochloride, peldesine, Peliomycin, Pelretin, Pelrinone Hydrochloride, Pemedolac, Pemerid Nitrate, pemirolast, Pemoline, Penamecillin, Penbutolol Sulfate, Penciclovir, Penfluridol, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfofamide, Perfosfamide, pergolide, Perhexyline Maleate, perillyl alcohol, Perindopril, perindoprilat, Perlapine, Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanyl ketoconazole, Phenylbutazone, Phenylephrine Hydrochloride, Phenylpropanolamine Hydrochloride, Phenylpropanolamine Polistirex, Phenyramidol Hydrochloride, Phenyloin, phosphatase inhibitors, Physostigmine, picenadol, picibanil, Picotrin Diolamine, picroliv, picumeterol, pidotimod, Pifamine, Pilocarpine, pilsicamide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin Sodium, Piperamide Maleate, piperazine, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretanide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Prenylamine, Pituitary, Posterior, Pivampicillin Hydrochloride, Pivopril, Pizotyline, placetin A, platinum compounds, platinum-triamine complex, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramiracetam Hydrochloride, Pramoxine Hydrochloride, Pranolium Chloride, Pravadoline Maleate, Pravastatin (Pravachol), Prazepam, Prazosin, Prazosin Hydrochloride, Prednazate, Prednicarbate, Prednimustine, Prednisolone, Prednisone, Prednival, Pregnenolone Succiniate, Prenalterol Hydrochloride, Pridefine Hydrochloride, Prifelone, Prilocalne Hydrochloride, Prilosec, Primaquine Phosphate, Primidolol, Primidone, Prinivil, prinomide Tromethamine, Prinoxodan, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin Human, Proline, Prolintane Hydrochloride, Promazine Hydrochloride, Promethazine Hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, L-, propiram, propiram+paracetamol, propiverine, Propofol, Propoxycaine Hydrochloride, Propoxyphene Hydrochloride, Propranolol Hydrochloride, Propulsid, propyl bis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, protosufloxacin, Protriptyline Hydrochloride, Proxazole, Proxazole Citrate, Proxicromil, Proxorphan Tartrate, prulifloxacin, Pseudoephedrine Hydrochloride, Puromycin, purpurins, Pyrabrom, Pyrantel, Pamoate, Pyrazinamide, Pyrazofurin, pyrazoloacridine, Pyridostigmine Bromide, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, PyrroInitrin, Pyrvinium Pamoate, Quadazocine Mesylate, Quazepam, Quazinone, Quazodine, Quazolast, quetiapine, quiflapon, quinagolide, Quinaldine Blue, quinapril, Quinaprilat, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole Sodium, Racephenicol, Racepinephrine, raf antagonists, Rafoxamide, Ralitoline, raloxifene, raltitrexed, ramatroban, Ramipril, Ramoplanin, ramosetron, ranelic acid, Ranimycin, Ranitidine, ranolazine, Rauwolfia Serpentina, recainam, Recainam Hydrochloride, Reclazepam, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retelliptine demethylated, reticulon, reviparin sodium, revizinone, rhenium Re 186 etidronate, rhizoxin, Ribaminol, Ribavirin, Riboprine, ribozymes, ricasetron, Ridogrel, Rifabutin, Rifametane, Rifamexil, Rifamide, Rifampin, Rifapentine, Rifaximin, retinamide, rilopirox, Riluzole, rimantadine, Rimcazole Hydrochloride, Rimexolone, Rimiterol Hydrobromide, rimoprogin, riodipine, Rioprostil, Ripazepam, ripisartan, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, ropinirole, Ropitoin Hydrochloride, ropivacaine, Ropizine, roquinimex, Rosaramicin, Rosoxacin, Rotoxamine, roxaitidine, Roxarsone, roxindole, roxithromycin, rubiginone Bi, ruboxyl, rufloxacin, rupatidine, Rutamycin, ruzadolane, Sabeluzole, safingol, safironil, saintopin, salbutamol, R—, Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, saquinavir, Sarafloxacin Hydrochloride, Saralasin Acetate, SarCNU, sarcophytol A, sargramostim, Sarmoxicillin, Sarpicillin, sarpogrelate, saruplase, saterinone, satigrel, satumomab pendetide, Schick Test Control, Scopafungin, Scopolamine Hydrobromide, Scrazaipine Hydrochloride, Sdi 1 mimetics, Secalciferol, Secobarbital, Seelzone, Seglitide Acetate, selegiline, Selegiline Hydrochloride, Selenium Sulfide, Selenomethionine Se 75, Selfotel, sematilide, semduramicin, semotiadil, semustine, sense oligonucleotides, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, setiptiline, Setoperone, sevirumab, sevoflurane, sezolamide, Sibopirdine, Sibutramine Hydrochloride, signal transduction inhibitors, Silandrone, silipide, silteplase, Silver Nitrate, simendan, Simtrazene, Simvastatin, Sincalide, Sinefungin, sinitrodil, sinnabidol, sipatrigine, sirolimus, Sisomicin, Sitogluside, sizofuran, sobuzoxane, Sodium Amylosulfate, Sodium Iodide I 123, Sodium Nitroprusside, Sodium Oxybate, sodium phenylacetate, Sodium Salicylate, solverol, Solypertine Tartrate, Somalapor, Somantadine Hydrochloride, somatomedin B, somatomedin C, somatrem, somatropin, Somenopor, Somidobove, sonermin, Sorbinil, Sorivudine, sotalol, Soterenol Hydrochloride, Sparfloxacin, Sparfosate Sodium, sparfosic acid, Sparsomycin, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin 1, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, stromelysin inhibitors, Strontium Chloride Sr 89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Suncillin Sodium, Suproclone, Suprofen, suradista, suramin, Surfomer, Suricamide Maleate, Suritozole, Suronacrine Maleate, Suxemerid Sulfate, swainsonine, symakalim, Symclosene, Symetine Hydrochloride, synthetic glycosaminoglycans, Taciamine Hydrochloride, Tacrine Hydrochloride, Tacrolimus, Talampicillin Hydrochloride, Taleranol, Talisomycin, tallimustine, Talmetacin, Talniflumate, Talopram Hydrochloride, Talosalate, Tametraline Hydrochloride, Tamoxifen, Tampramine Fumarate, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Technetium Tc 99 m Bicisate, Teclozan, Tecogalan Sodium, Teecleukin, Teflurane, Tegafur, Tegretol, Teicoplanin, telenzepine, tellurapyrylium, telmesteine, telmisartan, telomerase inhibitors, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, Tenidap, Teniposide, tenosal, tenoxicam, tepirindole, Tepoxalin, Teprotide, terazosin, Terbinafine, Terbutaline Sulfate, Terconazole, terfenadine, terflavoxate, terguride, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thimerfonate Sodium, Thimerosal, thiocoraline, thiofedrine, Thioguanine, thiomarinol, Thiopental Sodium, thioperamide, Thioridazine, Thiotepa, Thiothixene, Thiphenamil Hydrochloride, Thiphencillin Potassium, Thiram, Thozalinone, Threonine, Thrombin, thrombopoietin, thrombopoietin mimetic, thymalfasin, thymopoietin receptor agonist, thymotrinan, Thyromedan Hydrochloride, Thyroxine 1 125, Thyroxine 1 131, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, tin ethyl etiopurpurin, Tinabinol, Timidazole, Tinzaparin Sodium, Tioconazole, Tiodazosin, Tiodonium Chloride, Tioperidone Hydrochloride, Tiopinac, Tiospirone Hydrochloride, Tiotidine, tiotropium bromide, Tioxidazole, Tipentosin Hydrochloride, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tobramycin, Tocamide, Tocamphyl, Tofenacin Hydrochloride, Tolamolol, Tolazamide, Tolazoline Hydrochloride, Tolbutamide, Tolcapone, Tolciclate, Tolfamide, Tolgabide, lamotrigine, Tolimidone, Tolindate, Tolmetin, Tolnaftate, Tolpovidone 1 131, Tolpyrramide, Tolrestat, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor, Tracazolate, trafermin, Tralonide, Tramadol Hydrochloride, Tramazoline Hydrochloride, trandolapril, Tranexamic Acid, Tranilast, Transcamide, translation inhibitors, traxanox, Trazodone Hydrochloride, Trazodone-HCL, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, Triclonide, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethobenzamide Hydrochloride, Trimethoprim, Trimetozine, Trimetrexate, Trimipramine, Trimoprostil, Trimoxamine Hydrochloride, Triolein 1 125, Triolein 1 131, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine ester, tropisetron, trospectomycin, trovafloxacin, trovirdine, Tryptophan, Tubercullin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valine, Valnoctamide, Valproate Sodium, Valproic Acid, valsartan, vamicamide, vanadeine, Vancomycin, vaminolol, Vapiprost Hydrochloride, Vapreotide, variolin B, Vasopressin, Vecuronium Bromide, velaresol, Velnacrine Maleate, venlafaxine, veradoline Hydrochloride, veramine, Verapamil Hydrochloride, verdins, Verilopam Hydrochloride, Verlukast, Verofylline, veroxan, verteporfin, Vesnarinone, vexibinol, Vidarabine, vigabatrin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Volazocine, voriconazole, vorozole, voxergolide, Warfarin Sodium, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, Xylose, yangambin, zabicipril, zacopride, zafirlukast, Zalcitabine, zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, zoledronic acid, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin, JTT-501 (PNU-182716) (Reglitazar), AR-H039122, MCC-555 (Netoglitazone), AR-H049020, Tesaglitazar), CS-011 (CI-1037), GW-409544x, KRP-297, RG-12525, BM-15.2054, CLX-0940, CLX-0921, DRF-2189, GW-1929, GW-9820, LR-90, LY-510929, NIP-221, NIP-223, JTP-20993, LY 29311 Na, FK 614, BMS 298585, R 483, TAK 559, DRF 2725 (Ragaglitazar), L-686398, L-168049, L-805645, L-054852, Demethyl asteriquinone B1 (L-783281), L-363586, KRP-297, P32/98, CRE-16336, EML-1625, pharmaceutically acceptable salts thereof, or a combination thereof.

Suitable bioactive agents may also include, for example, leuprolide, octreotide, brimonidine, latanoprost, latanoprost acid, travoprost, travoprost acid, brinzolamide, dorzolamide, betaxolol, terbinafine, risperidone, rapamycin, or a combination thereof.

The bioactive agent, a metabolite, or a prodrug thereof, may be lyophilized prior to use. Typically, the bioactive agent, a metabolite, or a prodrug thereof, may be dissolved in an aqueous solution, sterile filtered, and lyophilized in a syringe. In a separate process, the thermoplastic polymer/biocompatible end-capped oligomeric liquid solution can be filled into a second syringe. The two syringes can be coupled together and the contents can be drawn back and forth between the two syringes until the thermoplastic polymer, biocompatible end-capped oligomeric liquid, and the bioactive agent, a metabolite, or a prodrug thereof, are effectively mixed together, forming a flowable composition. The flowable composition can be drawn into one syringe. The two syringes can be disconnected and a needle attached to the syringe containing the flowable composition. The flowable composition can be injected through the needle into the body. The flowable composition can be formulated and administered to a patient as described in, e.g., U.S. Pat. Nos. 5,312,519, 4,938,763, 5,702, 716, 5,744,153, and 5,990,194; or as described herein. Once administered, the biocompatible end-capped oligomeric liquid dissipates, the remaining polymer gels or solidifies, and a matrix structure is formed. The biocompatible end-capped oligomeric liquid should dissipate and the polymer should solidify or gel so as to entrap or encase the bioactive agent, a metabolite, or a prodrug thereof, within the matrix.

The release of bioactive agent from the implant should follow the same general rules for release of a drug from a monolithic polymeric device. The release of bioactive agent can be affected by the size and shape of the implant, the loading of bioactive agent within the implant, the permeability factors involving the bioactive agent, a metabolite, or a prodrug thereof, and the particular polymer, and the degradation of the polymer. Depending upon the amount of bioactive agent selected for delivery, the above parameters can be adjusted by one skilled in the art of drug delivery to give the desired rate and duration of release.

The amount of bioactive agent incorporated into the sustained release delivery system depends upon the desired release profile, the concentration of bioactive agent required for a biological effect, and the length of time that the bioactive agent, a metabolite, or a prodrug thereof, has to be released for treatment. There is no upper limit on the amount of bioactive agent incorporated into the sustained release delivery system except for that of an acceptable solution or dispersion viscosity for injection through a syringe needle. The lower limit of bioactive agent incorporated into the sustained release delivery system is dependent upon the activity of the bioactive agent, a metabolite, or a prodrug thereof, and the length of time needed for treatment. Specifically, in one embodiment, the sustained release delivery system can be formulated to provide a one month release of bioactive agent. In such an embodiment, the bioactive agent, a metabolite, or a prodrug thereof, can preferably be present in about 0.5 wt. % to about 50 wt. %, preferably about 1 wt. % to about 30 wt. % of the composition. Alternatively, in another embodiment, the sustained release delivery system can be formulated to provide a three month delivery of bioactive agent. In such an embodiment, the bioactive agent, a metabolite, or a prodrug thereof, can preferably be present in about 0.5 wt. % to about 50 wt. %, preferably about 1 wt. % to about 30 wt. % of the composition. The gel or solid implant formed from the flowable composition should release the bioactive agent, a metabolite, or a prodrug thereof, contained within its matrix at a controlled rate until the implant is effectively depleted of bioactive agent.

Adjuvants and Carriers

The sustained release delivery system may include a release rate modifier to alter the sustained release rate of bioactive agent from the implant matrix. The use of a release rate modifier may either decrease or increase the release of bioactive agent in the range of multiple orders of magnitude (e.g., 1 to 10 to 100), preferably up to a ten-fold change, as compared to the release of bioactive agent from an implant matrix without the release rate modifier.

With the addition of a hydrophobic release rate modifier, for example, hydrophobic ethyl heptanoate, to the sustained release delivery system, and formation of the implant matrix through interaction of the flowable composition and body fluid, the release rate of bioactive agent can be slowed. Hydrophilic release rate modifiers, for example, polyethylene glycol may increase the release of the bioactive agent, a metabolite, or a prodrug thereof. By an appropriate choice of the polymer molecular weight in combination with an effective amount of the release rate modifier, the release rate and extent of release of a bioactive agent, a metabolite, or a prodrug thereof, from the implant matrix may be varied, for example, from relatively fast to relatively slow.

Useful release rate modifiers include, for example, organic substances, which are water-soluble, water-miscible, or water insoluble (i.e., hydrophilic to hydrophobic).

The release rate modifier is preferably an organic compound, which is thought to increase the flexibility and ability of the polymer molecules and other molecules to slide past each other even though the molecules are in the solid or highly viscous state. Such an organic compound preferably includes a hydrophobic and a hydrophilic region. It is preferred that a release rate modifier is compatible with the combination of polymer and biocompatible end-capped oligomeric liquid used to formulate the sustained release delivery system. It is further preferred that the release rate modifier is a pharmaceutically-acceptable substance.

Useful release rate modifiers include, for example, fatty acids, triglycerides, other like hydrophobic compounds, organic liquids, plasticizing compounds, and hydrophilic compounds. Suitable release rate modifiers include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl)sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$-$C_{12}$ alkanols, 2-ethoxyethanol, and the like. The release rate modifier may be used singly or in combination with other such agents. Suitable combinations of release rate modifiers include, for example, glycerin/propylene glycol, sorbitol/glycerin, ethylene oxide/propylene oxide, butylene glycol/adipic acid, and the like. Preferred release rate modifiers include dimethyl citrate, triethyl citrate, ethyl heptanoate, glycerin, and hexanediol.

The amount of the release rate modifier included in the flowable composition should vary according to the desired rate of release of the bioactive agent, a metabolite, or a prodrug thereof, from the implant matrix. Preferably, the sustained release delivery system contains about 0.5 to about 30%, preferably about 5 to about 10%, of a release rate modifier.

Other solid adjuvants may also be optionally combined with the sustained release delivery system to act as carriers, especially isolation carriers. These include additives or excipients, for example, a starch, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, and/or polyvinylpyrrolidone.

Additional adjuvants may include oils, for example, peanut oil, sesame oil, cottonseed oil, corn oil, and olive oil as well as esters of fatty acids such as ethyl oleate, isopropyl myristate, fatty acid glycerides, and acetylated fatty acid glycerides. Also included are alcohols, for example, ethanol, isopropyl alcohol, hexadecyl alcohol, glycerol, and propylene glycol. Ethers, for example, poly(ethyleneglycol); petroleum hydrocarbons, for example, mineral oil and petrolatum may also be used in the formulations. Pectins, carbomers, methyl cellulose, hydroxypropyl cellulose, hydroxypropyl methyl cellulose, or carboxymethyl cellulose may also be included. These compounds can serve as isolation carriers by coating the bioactive agent, a metabolite, or a prodrug thereof, thereby preventing its contact with the biocompatible end-capped oligomeric liquid and other ingredients of the flowable composition. As isolation carriers, these compounds also help lower the burst effect associated with the coagulation of the flowable composition in situ.

Optionally, other compounds, for example, stabilizers, antimicrobial agents, antioxidants, pH modifiers, bioavailability modifiers, and combinations of these are included. Emulsifiers and surfactants, for example, fatty acids or a non-ionic surfactants including natural or synthetic polar oil, fatty acid esters, polyol ethers, and mono-, di-, or tri-glycerides may also be included.

The Implant

When the implant is formed, the implant has the physical state of a solid or a gel. The solid embodiments may be rigid so that they cannot be flexed or bent by squeezing them between the fingers or they may be flexible or bendable so that they can be compressed or flexed out of original shape by squeezing between the fingers (i.e., a low amount of force). The gel embodiments may be jelly-like in consistency and should flow under pressure. The thermoplastic polymer functions as a matrix in these embodiments to provide integrity to the single body solid or gel and to enable controlled release of the bioactive agent, a metabolite, or a prodrug thereof, upon implantation.

The thermoplastic polymer matrix is preferably a solid matrix and especially preferably is microporous. In an embodiment of the microporous solid matrix, there is a core surrounded by a skin. The core preferably contains pores of diameters from about 1 to about 1000 microns. The skin preferably contains pores of smaller diameters than those of the core pores. In addition, the skin pores are preferably of a size such that the skin is functionally non-porous in comparison with the core.

Because all of the components of the implant are biodegradable or can be swept away from the implant site by body fluid and eliminated from the body, the implant eventually disappears. Typically the implant components complete their biodegradation or disappearance after the bioactive agent, a metabolite, or a prodrug thereof, has been typically completely released. The structure of the thermoplastic polymer, its molecular weight, the density and porosity of the implant, and the body location of the implant all affect the biodegradation and disappearance rates.

The implant is typically formed subcutaneously in a patient. It can be molded in place upon injection to provide comfort to the patient. The implant volume typically may be between about 0.25 mL and about 3 mL in size.

Therapeutic Use

In general, any disease, which may be ameliorated, treated, cured, or prevented by administration of a bioactive agent, a metabolite, or a prodrug thereof, may be treated by administration of the flowable compositions.

Dosages

The amount of flowable composition administered should typically depend upon the desired properties of the controlled release implant. For example, the amount of flowable composition can influence the length of time in which the bioactive agent, a metabolite, or a prodrug thereof, is released from the controlled release implant. Specifically, in one embodiment, the composition can be used to formulate a one month delivery system of bioactive agent. In such an embodiment, about 0.20 mL to about 2.0 mL of the flowable composition can be administered. Alternatively, in another embodiment, the composition can be used to formulate a three month delivery system of bioactive agent. In such an embodiment, about 0.75 mL to about 1.0 mL of the flowable composition can be administered.

The amount of bioactive agent within the flowable composition and the resulting implant should depend upon the disease to be treated, the length of duration desired and the bioavailability profile of the implant. Generally, the effective amount should be within the discretion and wisdom of the patient's attending physician. The injection volume of the typical flowable composition should range from 0.2 to 2.0 mL per implant. The polymer formulation should be the primary factor for obtaining the longer sustained release, as discussed above.

All publications, patents, and patent documents are incorporated by reference herein, as though individually incorporated by reference. The invention should now be illustrated with the following non-limiting examples.

EXAMPLES

The ATRIGEL® drug delivery system is a biodegradable polymeric delivery system that can be injected as a liquid. Upon injection of the formulation, the polymer solidifies encapsulating the drug. As the process of biodegradation begins, the drug is slowly released. The release rate of drugs from this type of delivery system can be controlled by the type and molecular weight of the polymer and drug load of the constituted product. Therefore, the system can be tailored to meet the needs of the patient.

The ATRIGEL® Delivery System is currently used in the Food and Drug Administration approved products ELIGARD™ (one, three, and four-month subcutaneous depot formulations of leuprolide acetate) and ATRIDOX® (doxycycline hyclate applied to the periodontal pocket). Clinical studies and post-marketing experience with these products demonstrate that the ATRIGEL® Delivery System itself is well tolerated and provides consistent, sustained release of the incorporated drug over the designated dosing period.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may inherently contain certain errors necessarily resulting from the standard deviation found in their respective testing measurements.

LIST OF ABBREVIATIONS AND DEFINITION OF TERMS

| | |
|---|---|
| 90/10 | Weight ratio of lactide to glycolide in the polymer |
| ATRIGEL ® | General name given to a solution prepared by dissolving poly(lactide-co-glycolide) polymers in a biocompatible solvent (typically NMP) |

-continued

LIST OF ABBREVIATIONS AND DEFINITION OF TERMS

| | |
|---|---|
| Max | Maximum |
| mg | Milligram |
| Min | Minimum |
| Min | Minute |
| mL | Milliliter |
| MW | Molecular Weight |
| NMP | N-methyl-2-pyrrolidone |
| PEG | Polyethylene glycol |
| PLA | Polylactide |
| PLG | Poly(lactide-co-glycolide) with methyl end group |
| PLC | Poly(lactide-co-caprolactone) |
| PLGH | Poly(DL-lactide-co-glycolide) with a carboxylic acid end group |
| PLGHp | Poly(DL-lactide-co-glycolide) with a free carboxylic acid group on at least one end of each polymer chain) that has been purified by a solvent/nonsolvent precipitation method. |
| RT | Room Temperature |

Example 1

Preparation of Ethyl Lactyllactate

This procedure was slightly modified from U.S. Pat. No. 2,371,281. 200 milliliters (mL) of anhydrous ethanol, 72 gram (g) of DL-lactide, and a trace amount (approximately 0.01 gram) benzenesulphonic acid were heated under reflux condenser under anhydrous conditions at 75° C. for twenty-four hours. The excess ethanol was removed by distillation and the residue was fractionally distilled under reduced pressure. The first fraction distilled at 40-110° C. at 10 millimeters (mm) mercury (Hg) and was believed to contain mostly ethanol. The second fraction distilled at 110-120° C. at 10 millimeters (mm) mercury (Hg) and was believed to contain ethanol and ethyl lactyllactate. At this time, the distillation was stopped. The reaction mixture remaining in the flask was isolated, tested by gas chromatography-mass spectroscopy (GC-MS), and found to consist mainly of ethyl lactyllactate.

Example 2

Preparation of Ethyl(glycoloyloxy)acetate

This procedure was slightly modified from U.S. Pat. No. 2,371,281. 200 milliliters (mL) of anhydrous ethanol, 72 gram (g) of glycolide, and a trace amount (approximately 0.01 gram) benzenesulphonic acid were heated under reflux condenser under anhydrous conditions at 75° C. for 24 hours. The excess ethanol was removed by distillation. The reaction mixture remaining in the flask was isolated, tested by gas chromatography-mass spectroscopy (GC-MS), and found to consist mainly of ethyl(glycoloyloxy)acetate.

Example 3

Preparation of n-Propyl Lactyllactate

This procedure was slightly modified from U.S. Pat. No. 2,371,281. 200 milliliters (mL) of n-propanol, 72 gram (g) of DL-lactide, and a trace amount (approximately 0.01 gram) benzenesulphonic acid were heated under reflux condenser under anhydrous conditions 75° C. for 24 hours. The reaction mixture remaining in the flask was isolated, tested by gas chromatography-mass spectroscopy (GC-MS), and found to consist mainly of n-propyl lactyllactate.

Example 4

Preparation of Mixture of 2-Hydroxypropyl Lactyllactate and 1-Methyl-2-Hydroxypropyl Lactyllactate This procedure was slightly modified from U.S. Pat. No. 2,371,281. 200 milliliters (mL) of 1,2-propanediol, 72 gram (g) of DL-lactide, and a trace amount (approximately 0.01 gram) benzenesulphonic acid were heated under reflux condenser under anhydrous conditions 75° C. for 24 hours. The reaction mixture remaining in the flask was isolated, tested by gas chromatography-mass spectroscopy (GC-MS), and found to consist mainly of a mixture of 2-hydroxypropyl lactyllactate and 1-methyl-2-hydroxypropyl lactyllactate.

Example 5

General Preparation of Ethyl Lactyllactate with Acetyl End Caps

Ethyl lactyllactate (1 mole) prepared by the procedure of Example 1 is added drop wise with stirring and under anhydrous conditions and inert atmosphere to acetyl chloride (2.2 mole) in anhydrous pyridine at 0° C. The reaction mixture is stirred at room temperature overnight. The reaction is worked up in the usual manner to afford ethyl lactyllactate with acetyl end caps.

Example 6

Preparation of Ethyl(glycoloyloxy)acetate with Acetyl End Caps

Ethyl(glycoloyloxy)acetate (1 mole) prepared by the procedure of Example 2 is added drop wise with stirring and under anhydrous conditions and inert atmosphere to acetyl chloride (2.2 mole) in anhydrous pyridine at 0° C. The reaction mixture is stirred at room temperature overnight. The reaction is worked up in the usual manner to afford ethyl (glycoloyloxy)acetate with acetyl end caps.

Example 7

Preparation of n-Propyl Lactyllactate with Acetyl End Caps n-Propyl Lactyllactate (1 mole) prepared by the procedure of Example 3 is added drop wise with stirring and under anhydrous conditions and inert atmosphere to acetyl chloride (2.2 mole) in anhydrous pyridine at 0° C. The reaction mixture is stirred at room temperature overnight. The reaction is worked up in the usual manner to afford n-propyl lactyllactate with acetyl end caps.

Example 8

Preparation of the Mixture of 2-Hydroxypropyl Lactyllactate with Acetyl End Caps and 1-Methyl-2-Hydroxypropyl Lactyllactate with Acetyl End Caps The mixture of 2-hydroxypropyl lactyllactate and 1-methyl-2-hydroxypropyl lactyllactate (1 mole) prepared by the procedure of Example 4 is added drop wise with stirring and under anhydrous conditions and inert atmosphere to acetyl chloride (2.2 mole) in anhydrous pyridine at 0° C. The reaction mixture is stirred at room temperature overnight. The reaction is worked up in the usual manner to afford a mixture of 2-hydroxypropyl lactyllactate with acetyl end caps and 1-methyl-2-hydroxypropyl lactyllactate with acetyl end caps.

Example 9

Preparation of Ethyl Lactyllactate with Propionyl End Caps

Ethyl lactyllactate (1 mole) prepared by the procedure of Example 1 is added drop wise with stirring and under anhydrous conditions and inert atmosphere to propionyl chloride (2.2 mole) in anhydrous pyridine at 0° C. The reaction mixture is stirred at room temperature overnight. The reaction is worked up in the usual manner to afford ethyl lactyllactate with propionyl end caps.

Example 10

Preparation of Ethyl(glycoloyloxy)acetate with Propionyl End Caps

Ethyl(glycoloyloxy)acetate (1 mole) prepared by the procedure of Example 2 is added drop wise with stirring and under anhydrous conditions and inert atmosphere to propionyl chloride (2.2 mole) in anhydrous pyridine at 0° C. The reaction mixture is stirred at room temperature overnight. The reaction is worked up in the usual manner to afford ethyl (glycoloyloxy)acetate with propionyl end caps.

Example 11

Preparation of n-Propyl Lactyllactate with Propionyl End Caps n-Propyl Lactyllactate (1 mole) prepared by the procedure of Example 3 is added drop wise with stirring and under anhydrous conditions and inert atmosphere to propionyl chloride (2.2 mole) in anhydrous pyridine at 0° C. The reaction mixture is stirred at room temperature overnight. The reaction is worked up in the usual manner to afford n-propyl lactyllactate with propionyl end caps.

Example 12

Preparation of the Mixture of 2-Hydroxypropyl Lactyllactate with Propionyl End Caps and 1-Methyl-2-Hydroxypropyl Lactyllactate with Propionyl End Caps The mixture of 2-hydroxypropyl lactyllactate and 1-methyl-2-hydroxypropyl lactyllactate (1 mole) prepared by the procedure of Example 4 is added drop wise with stirring and under anhydrous conditions and inert atmosphere to propionyl chloride (2.2 mole) in anhydrous pyridine at 0° C. The reaction mixture is stirred at room temperature overnight. The reaction is worked up in the usual manner to afford a mixture of 2-hydroxypropyl lactyllactate with propionyl end caps and 1-methyl-2-hydroxypropyl lactyllactate with propionyl end caps.

Example 13

Preparation of Ethyl Lactyllactate with Butyryl End Caps

Ethyl lactyllactate (1 mole) prepared by the procedure of Example 1 is added drop wise with stirring and under anhydrous conditions and inert atmosphere to butyryl chloride (2.2 mole) in anhydrous pyridine at 0° C. The reaction mixture is stirred at room temperature overnight. The reaction is worked up in the usual manner to afford ethyl lactyllactate with butyryl end caps.

Example 14

Preparation of Ethyl(glycoloyloxy)acetate with Butyryl End Caps

Ethyl(glycoloyloxy)acetate (1 mole) prepared by the procedure of Example 2 is added drop wise with stirring and under anhydrous conditions and inert atmosphere to butyryl chloride (2.2 mole) in anhydrous pyridine at 0° C. The reaction mixture is stirred at room temperature overnight. The reaction is worked up in the usual manner to afford ethyl (glycoloyloxy)acetate with butyryl end caps.

Example 15

Preparation of n-Propyl Lactyllactate with Butyryl End Caps n-Propyl Lactyllactate (1 mole) prepared by the procedure of Example 3 is added drop wise with stirring and under anhydrous conditions and inert atmosphere to butyryl chloride (2.2 mole) in anhydrous pyridine at 0° C. The reaction mixture is stirred at room temperature overnight. The reaction is worked up in the usual manner to afford n-propyl lactyllactate with butyryl end caps.

Example 16

Preparation of the Mixture of 2-Hydroxypropyl Lactyllactate with Butyryl End Caps and 1-Methyl-2-Hydroxypropyl Lactyllactate with Butyryl End Caps The mixture of 2-hydroxypropyl lactyllactate and 1-methyl-2-hydroxypropyl lactyllactate (1 mole) prepared by the procedure of Example 4 is added drop wise with stirring and under anhydrous conditions and inert atmosphere to butyryl chloride (2.2 mole) in anhydrous pyridine at 0° C. The reaction mixture is stirred at room temperature overnight. The reaction is worked up in the usual manner to afford a mixture of 2-hydroxypropyl lactyllactate with butyryl end caps and 1-methyl-2-hydroxypropyl lactyllactate with butyryl end caps.

Concentrations, amounts, percentages, time periods, etc., of various components or use or effects of various components of this invention, including but not limited to the flowable composition, implants, indications of reduction in malcondition symptoms, and treatment time periods, are often presented in a range or baseline threshold format throughout this document. The description in range or baseline threshold format is merely for convenience and brevity and should not be construed as an inflexible limitation on the scope of the invention. Accordingly, the description of a range or baseline threshold should be considered to have specifically disclosed all the possible subranges as well as individual numerical values within that range or above that baseline threshold. For example, description of about 0.5 wt. % to about 50 wt. % of a bioactive agent should be considered to have specifically disclosed subranges, such as about 0.75 wt. % to about 45 wt. %, about 1 wt. % to about 30 wt. %, about 5 wt. % to about 20 wt. %, etc., as well as individual numbers within that range, such as about 5 wt. %, about 10 wt. %, about 30 wt. %, etc. This construction applies regardless of the breadth of the range or baseline threshold and in all contexts throughout this disclosure.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

What is claimed is:

1. A flowable composition comprising:
(i) a biodegradable thermoplastic polymer that is at least substantially insoluble in body fluid,
wherein the polymer is a poly(DL-lactide-co-glycolide) (PLG) without a carboxy terminal group, wherein the polymer without a terminal carboxyl group is optionally extended with a $C_2$ to $C_{12}$ diol and wherein the biodegradable thermoplastic polymer is a non-hydrolyzed PLG low-burst copolymer polyester material having a weight average molecular weight of about 10 kilodaltons to about 50 kilodaltons, a polydispersity index of about 1.4 to about 2.0, and from which a copolymer fraction having a weight average molecular weight of about 4 kDa to about 10 kDa and a polydispersity index of about 1.4 to about 2.5 has been removed;
(ii) a biocompatible end-capped oligomeric liquid at ambient temperature of the formula I, II, III, IV, or V:

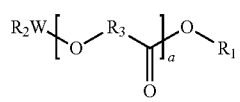

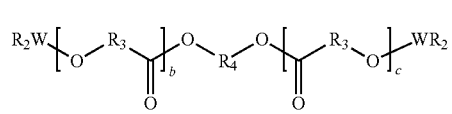

-continued

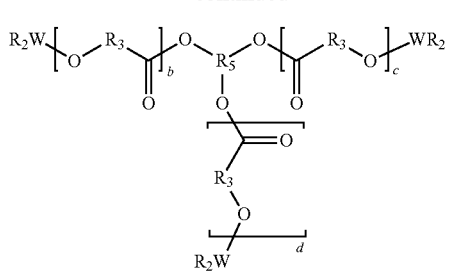

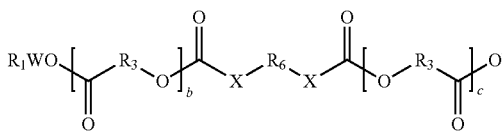

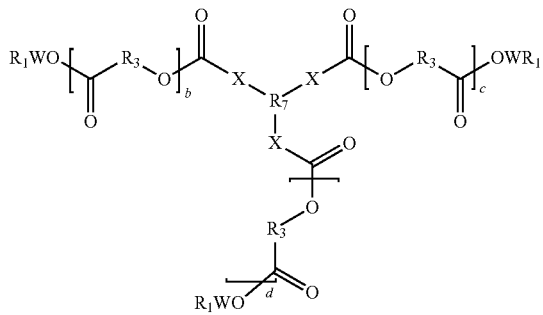

wherein:
each $R_1$ is independently $(C_1-C_{12})$alkyl, or $(C_1-C_{12})$alkylenecarboxylic$(C_1-C_{12})$alkylester;
each $R_2$ is independently $(C_1-C_{12})$alkyl, carbonyl$(C_1-C_{12})$alkyl, or carboxylic$(C_1-C_{12})$alkylester;
each $R_3$ is independently $(C_1-C_{12})$alkylene;
$R_4$ is $(C_1-C_{12})$alkylene, carbonyl$(C_1-C_{12})$alkylcarbonyl, or $(C_3-C_{12})$cycloalkadiyl;
$R_5$ is $(C_1-C_{12})$alkatriyl or $(C_3-C_{12})$cycloalkatriyl;
$R_6$ is $(C_1-C_{12})$alkylene, $(C_1-C_{12})$alkyne, $(C_3-C_{12})$cycloalkadiyl, $(C_1-C_{12})$alkatriyl, or $(C_3-C_{12})$cycloalkatriyl;
$R_7$ is $(C_1-C_{12})$alkylene or $(C_1-C_{12})$alkatriyl,
X is absent or oxygen;
W is absent, carbonyl, carbonyloxy, or oxycarbonyl; and
any alkyl or alkylene of $R_1$, $R_2$, $R_3$, $R_4$, $R_5$, $R_6$ and $R_7$ can optionally be substituted on carbon with one or more oxo, hydroxy, halogen, nitro, cyano, $(C_1-C_{12})$alkyl, $(C_1-C_6)$alkoxy, trifluoromethyl, and optionally interrupted on carbon with one or more oxy, imino, or thio, and is optionally partially unsaturated; and
each a, b, c, and d is independently 0, 1, 2, 3, 4, or 5;
wherein the oligomeric liquid is of low water solubility to water insolubility, forming an aqueous solution of no more than 5% by weight in water; and
(iii) a bioactive agent, a metabolite, or a prodrug thereof;
wherein the composition does not comprise an organic solvent or an oligomeric liquid comprising free carboxyl and free hydroxyl groups.

2. The flowable composition of claim 1, wherein
each $R_1$ is independently $-(CH_2)_mCH_3$, $-CH_2CH_2(OCH_2CH_2)_mO(CH_2)_nCH_3$, $-CH_2CH_2(OCH_2CH_2)_mOCOCH_3$, $-CH_2COOY$, $-CH(CH_3)COOY$, $-CH_2CH_2COOY$, $-CH_2CH_2CH_2COOY$, $-CH_2CH_2CH_2CH_2COOY$, $-CH_2CH_2CH_2CH_2CH_2COOY$, $-CH_2CH(CH_3)Y$, or $-(cycloC_6H_{11})-$, wherein each m and n is independently 0, 1, 2, 3, 4, 5, 6, or 7;
each $R_2$ is independently $-CH_3$, $-CH_2CH_3$, $-(CH_2)_oCH_3$, $-CH_2CH_2(OCH_2CH_2)_oCH_3$, $-CH_2CH_2(OCH_2CH_2)_oOCH_2CH_3$, $-CH_2CH_2(OCH_2CH_2)_oOCOCH_3$, $-COCH_3$, $-CO(CH_2)_oCH_3$, $-COO(CH_2)_oCH_3$, or $-CO(OCH_2CH_2)_oCH_3$, wherein o is 0, 1, 2, 3, 4, 5, 6, or 7;
each $R_3$ is independently $-(CH_2)_p-$, $-CH(CH_3)-$, $-(CH_2CH_2O)_pCH_2-$, $-(CH(CH_3)CH_2)-$, or $-(CH(CH_2CH_3)CH_2)-$, wherein p is 0, 1, 2, 3, 4, 5, 6, or 7, $R_4$ is $-(CH_2)_q-$, $-CO(CH_2)_qCO-$, $-(CH_2CH_2O)_qCH_2CH_2-$, $-CH_2CH_2CH_2CH_2CH_2CH_2-$, $-(CH_2)_qCH(CH_3)-$, $-((CH_2)_qO)_q$, $-CH_2CH(Y)CH_2-$, cyclohexane-1,2-diyl, cyclohexane-1,3-diyl or cyclohexane-1,4-diyl, wherein q is 1, 2, 3, 4, 5, 6, or 7;
$R_5$ is $(-CH_2)_2CH-$, $(-CH_2)_3CCH_3$, $(-CH_2)_3CCH_2CH_3$, or 1,2,6-hexanetriyl;
$R_6$ is $-CH=CH-$, $-(CH_2)_r-$, $-O(CH_2CH_2O)_r-$ wherein r is 1, 2, 3, 4, 5, 6, or 7;
$R_7$ is $(-CH_2)_2CH-$, $(-CH_2)_2COH-$, $(-CH_2)(-CHOH)CH-$, $(-CH_2)(-CO)CH-$, or $(-CH_2)(-CH=)C-$;
X is absent or oxygen;
W is absent, $-CO-$, $-COO-$, or $-OCO-$; and
Y is $-CH_3$, $-C_2H_5$, $-C_3H_7$, or $-C_4H_9$.

3. The flowable composition of claim 2, wherein
each $R_1$ is independently $-CH_3$, $-CH_2CH_3$, $-(CH_2)_2CH_3$, $-(CH_2)_3CH_3$, $-(CH_2)_4CH_3$, $-(CH_2)_5CH_3$, $-(CH_2)_6CH_3$, $-(CH_2)_7CH_3$, $-CH_2CH_2(OCH_2CH_2)_{20}CH_3$, $-CH_2CH_2(OCH_2CH_2)_2OCH_2CH_3$, or $-CH_2CH_2(OCH_2CH_2)_2OCOCH_3$;
each $R_2$ is independently $-CH_3$, $-CH_2CH_3$, $-(CH_2)_2CH_3$, $-(CH_2)_3CH_3$, $-(CH_2)_4CH_3$, $-(CH_2)_5CH_3$, $-(CH_2)_6CH_3$, $-(CH_2)_7CH_3$, $-CH_2CH_2(OCH_2CH_2)_{20}CH_3$, $-CH_2CH_2(OCH_2CH_2)_2OCH_2CH_3$, or $-CH_2CH_2(OCH_2CH_2)_2OCOCH_3$;
each $R_3$ is independently $-CH_2-$, $-(CH_2)_2-$, $-(CH_2)_3-$, $-(CH_2)_4-$, $-(CH_2)_5-$, $-(CH_2)_6-$, $-(CH_2)_7-$, $-CH(CH_3)-$, $-(CH(CH_3)CH_2)-$, $-(CH(CH_2CH_3)CH_2)-$, or $-(CH_2CH_2OCH_2)-$;
$R_4$ is $-(CH_2)_3-$, $-(CH_2)_4-$, $-(CH_2)_5-$, $-(CH_2)_6-$, $-COCH_2CO-$, $-CO(CH_2)_2CO-$, $-CO(CH_2)_3CO-$, $-CO(CH_2)_4CO-$, $-CO(CH_2)_5CO-$, $-CO(CH_2)_6CO-$, $-CO(CH_2)_7CO-$, $-CO(CH_2)_8CO-$, $-(CH_2CH_2O)_2CH_2CH_2-$, $-(CH_2CH_2O)_3CH_2CH_2-$, $-(CH_2CH_2O)_4CH_2CH_2-$, $-(CH_2CH_2O)_5CH_2CH_2-$, $-(CH_2CH_2O)_6CH_2CH_2-$, or $-CH_2CH_2CH_2CH_2CH_2CH_2-$;
$R_5$ is $(-CH_2)_2CH-$;
$R_6$ is $-CH=CH-$, $-(CH_2)-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-O(CH_2CH_2O)-$, $-O(CH_2CH_2O)_2-$, $-O(CH_2CH_2O)_3-$, $-O(CH_2CH_2O)_4-$, $-O(CH_2CH_2O)_5-$, or $-O(CH_2CH_2O)_6-$;
$R_7$ is $(-CH_2)_2CH-$, $(-CH_2)_2COH-$, $(-CH_2)(-CHOH)CH-$, $(-CH_2)(-CO)CH-$, or $(-CH_2)(-CH=)C-$;
X is absent or oxygen;
W is absent, $-CO-$, $-COO-$, or $-OCO-$; and
each a, b, c, and d is independently 0, 1, 2, 3, or 4.

4. The flowable composition of claim 1, wherein the biocompatible end-capped oligomeric liquid is present in about 10 wt. % to about 30 wt. % of the composition.

5. The flowable composition of claim 1, wherein the biodegradable thermoplastic polyester is present in about 10 wt. % to about 95 wt. %, and optionally the biodegradable thermoplastic polyester has an average molecular weight of from about 10,000 to about 45,000 Daltons.

6. The flowable composition of claim 1, wherein the bioactive agent, a metabolite, or a prodrug thereof, comprises a hormone, an immunomodulator, an immunosuppressant, an antibiotic, a cytostatic, a diuretic, a gastrointestinal agent, a cardiovascular agent, a neuropharmaceutical, or a combination thereof.

7. The flowable composition of claim 1, wherein the bioactive agent, a metabolite, or a prodrug thereof, comprises leuprolide, octreotide, brimonidine, latanoprost, latanoprost acid, travoprost, travoprost acid, brinzolamide, dorzolamide, betaxolol, terbinafine, risperidone, rapamycin, or a combination thereof.

8. The composition of claim 7, wherein the bioactive agent, a metabolite, or a prodrug thereof, is present in about 0.1 wt. % to about 50 wt. % of the composition.

9. The flowable composition of claim 1, further comprising a biocompatible polar aprotic organic liquid comprising N-methyl-2-pyrrolidone, 2-pyrrolidone, N,N-dimethylformamide, dimethyl sulfoxide, propylene carbonate, caprolactam, triacetin, or any combination thereof.

10. The flowable composition of claim 1, that is an injectable subcutaneous formulation, and optionally has a volume of about 0.20 mL to about 2.0 mL.

11. The flowable composition of claim 10, that is formulated for administration about once per month.

12. The flowable composition of claim 1, having the property of production of minimal tissue necrosis when injected subcutaneously.

13. The flowable composition of claim 1, having a substantially linear cumulative release profile after one day.

14. A biodegradable implant formed in situ, in a patient, by the steps comprising:
   injecting a composition of claim 1 into the body of the patient; and
   allowing the biocompatible end-capped oligomeric liquid to dissipate to produce a solid or gel biodegradable implant.

15. The implant of claim 14, wherein the implant has a solid or gelatinous matrix, and the matrix being a core surrounded by a skin; or wherein the implant is solid and microporous.

16. The implant of claim 15, wherein the core contains pores of diameters from about 1 to about 1000 microns, and optionally the skin contains pores of smaller diameters than those of the core pores, and optionally the skin pores are of a size such that the skin is functionally non-porous in comparison with the core.

* * * * *